(12) United States Patent
Caprioli

(10) Patent No.: US 7,799,519 B2
(45) Date of Patent: Sep. 21, 2010

(54) DIAGNOSING AND GRADING GLIOMAS USING A PROTEOMICS APPROACH

(75) Inventor: Richard Caprioli, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 1108 days.

(21) Appl. No.: 11/428,755

(22) Filed: Jul. 5, 2006

(65) Prior Publication Data

US 2007/0031900 A1 Feb. 8, 2007

Related U.S. Application Data

(60) Provisional application No. 60/697,083, filed on Jul. 7, 2005.

(51) Int. Cl.
C12Q 1/00 (2006.01)
G01N 33/53 (2006.01)

(52) U.S. Cl. .......................... 435/4; 435/7.1

(58) Field of Classification Search ...................... None
See application file for complete search history.

(56) References Cited

U.S. PATENT DOCUMENTS

2002/0155480 A1* 10/2002 Golub et al. ................. 435/6

FOREIGN PATENT DOCUMENTS

WO WO 0033083 A1 * 6/2000
WO WO 03025138 A2 * 3/2003

OTHER PUBLICATIONS

Alizadeh et al., "Distinct types of diffuse large B-cell lymphoma identified by gene expression profiling," *Nature* 403(6769):503-511, 2000.
Bittner et al., "Molecular classification of cutaneous malignant melanoma by gene expression profiling," *Nature* 406 (6795), 536-40, 2000.
Bronckart et al., "Development and progression of malignancy in human colon tissues are correlated with expression of specific Ca(2+)-binding S100 proteins," *Histol. Histopathol.*, 16:707-712, 2001.
Caldwell and Caprioli, "Tissue profiling by mass spectrometry: a review of methodology and applications," *Mol. Cell. Proteomics*, 4(4):394-401, 2005.
Camby et al., "Supratentorial pilocytic astrocytomas, astrocytomas, anaplastic astrocytomas and glioblastomas are characterized by a differential expression of S100 proteins," *Brain Pathol.*, 9:1-19, 1999.
Caprioli., "Deciphering protein molecular signatures in cancer tissues to aid in diagnosis, prognosis, and therapy," *Cancer Research*, 65(23):10642-10645, 2005.
Chaurand et al., "Integrating histology and imaging mass spectrometry," *Anal. Chem.*, 76(4):1145-1155, 2004.
Chaurand et al., "Proteomics in diagnostic pathology: profiling and imaging proteins directly in tissue sections," *Am. J. Pathol.*, 165(4):1057-1068, 2004.

Condorelli et al., "PED/PEA-15 gene controls glucose transport and is overexpressed in type 2 diabetes mellitus," *Embo J.*, 17:3858-3866, 1998.
Condorelli et al., "PED/PEA-15: an anti-apoptotic molecule that regulates FAS/TNFR1-induced apoptosis," *Oncogene*, 18:4409-4415, 1999.
Dougherty, "Small sample issues for microarray-based classification," *Comparative and Functional Genomics* 2:28-34, 2001.
El-Rifai et al., "Gastric cancers overexpress S100A calcium-binding proteins," *Cancer Res.*, 62:6823-6826, 2002.
Golub et al., "Molecular classification of cancer: class discovery and class prediction by gene expression monitoring," *Science* 286, 531-537, 1999.
Komatsu et al., "Expression of S100A6 and S100A4 in matched samples of human colorectal mucosa, primary colorectal adenocarcinomas and liver metastases," *Oncology*, 63:192-200, 2002.
Melki et al., "Cofactor A is a molecular chaperone required for beta-tubulin folding: functional and structural characterization," *Biochemistry*, 35:10422-10435, 1996.
Puthalakath et al., "The proapoptotic activity of the Bcl-2 family member Bim is regulated by interaction with the dynein motor complex," *Mol. Cell*, 3:287-296, 1999.
Ramos et al., "Death effector domain protein PEA-15 potentiates Ras activation of extracellular signal receptor-activated kinase by an adhesion-independent mechanism," *Mol. Biol. Cell*, 11:2863-2872, 2000.
Schwartz et al., "Protein profiling in brain tumors using mass spectrometry: feasibility of a new technique for the analysis of protein expression," *Clin. Cancer Res.*, 10(3):981-987, 2004.
Schwartz et al., "Proteomic-based prognosis of brain tumor patients using direct-tissue matrix-assisted laser desorption ionization mass spectrometry," *Cancer Res.*, 65(17):7674-7681, 2005.
Stoeckli et al., "Imaging mass spectrometry: a new technology for the analysis of protein expression in mammalian tissues," *Nat. Med.*, 7(4):493-496, 2001.
Stulik et al., "Differential expression of the Ca2+ binding S100A6 protein in normal, preneoplastic and neoplastic colon mucosa," *Eur. J. Cancer*, 36:1050-1059, 2000.
Tonini et al., "Gene expression and protein localisation of calcyclin, a calcium-binding protein of the S-100 family in fresh neuroblastomas," *Eur. J. Cancer*, 31A:499-504, 1995.
Vaarala et al., "Differentially expressed genes in two LNCaP prostate cancer cell lines reflecting changes during prostate cancer progression," *Lab. Invest.*, 80:1259-1268, 2000.
Zhang et al., "RNA interference-mediated silencing of the S100A10 gene attenuates plasmin generation and invasiveness of Colo 222 colorectal cancer cells," *J. Biol. Chem.*, 279:2053-2062, 2004.
Zhi et al., "The deregulation of arachidonic acid metabolism-related genes in human esophageal squamous cell carcinoma," *Int. J. Cancer*, 106:327-333, 2003.

* cited by examiner

*Primary Examiner*—Larry R Helms
*Assistant Examiner*—Hong Sang
(74) *Attorney, Agent, or Firm*—Fulbright & Jaworski

(57) ABSTRACT

The present invention provides for a proteomic approach to grading gliomas, and for predicting patient survival. In addition to employing global protein expression patterns, such as by mass spectrometry, particular target proteins whose expression is altered in various gliomas can be used to predict the stage/classification of a glioma, as well as to indicate whether a given patient will be a short- or long-term survivor.

35 Claims, 5 Drawing Sheets

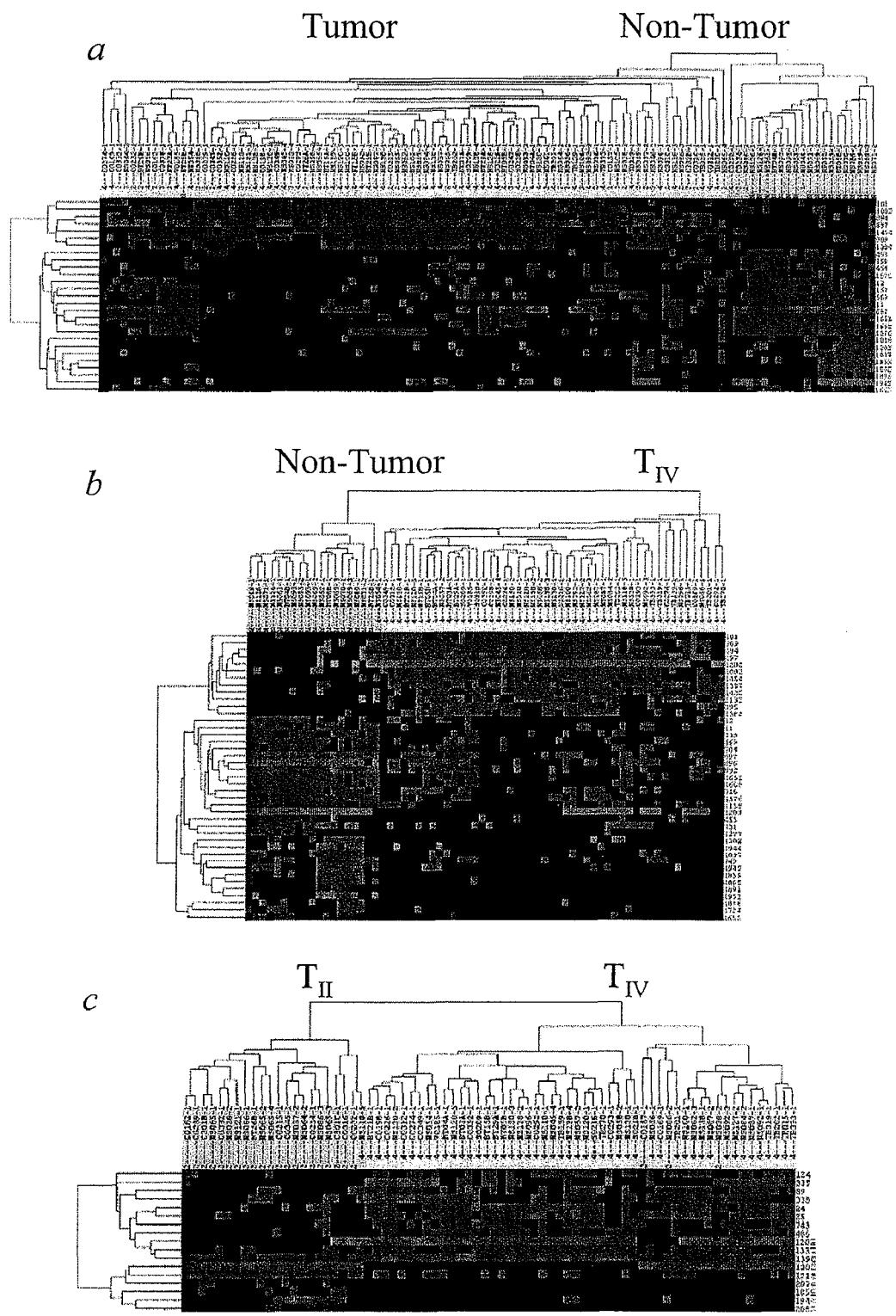
FIG. 3A-C

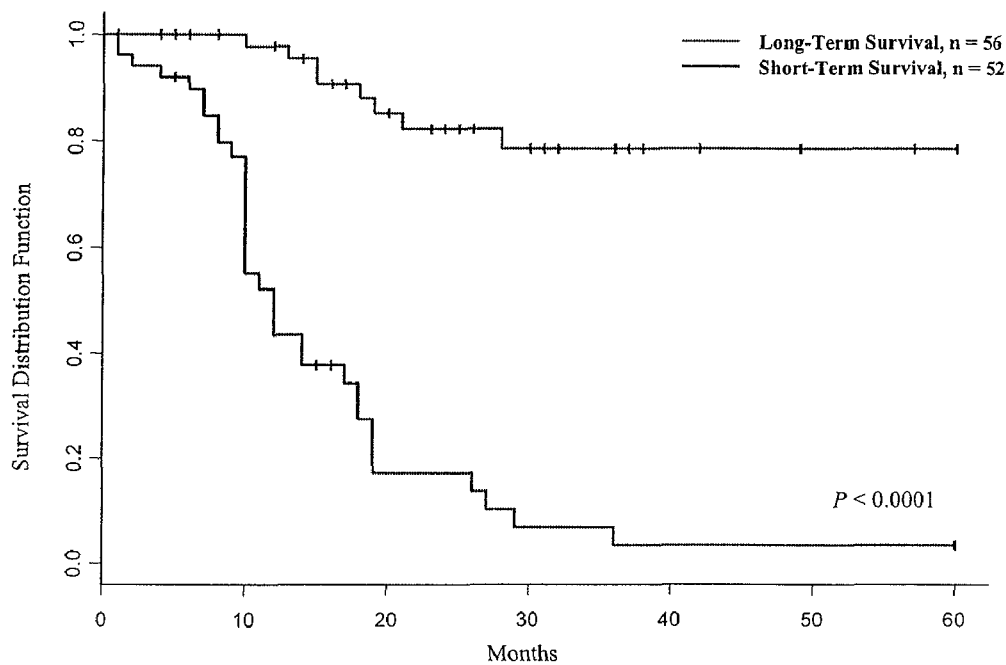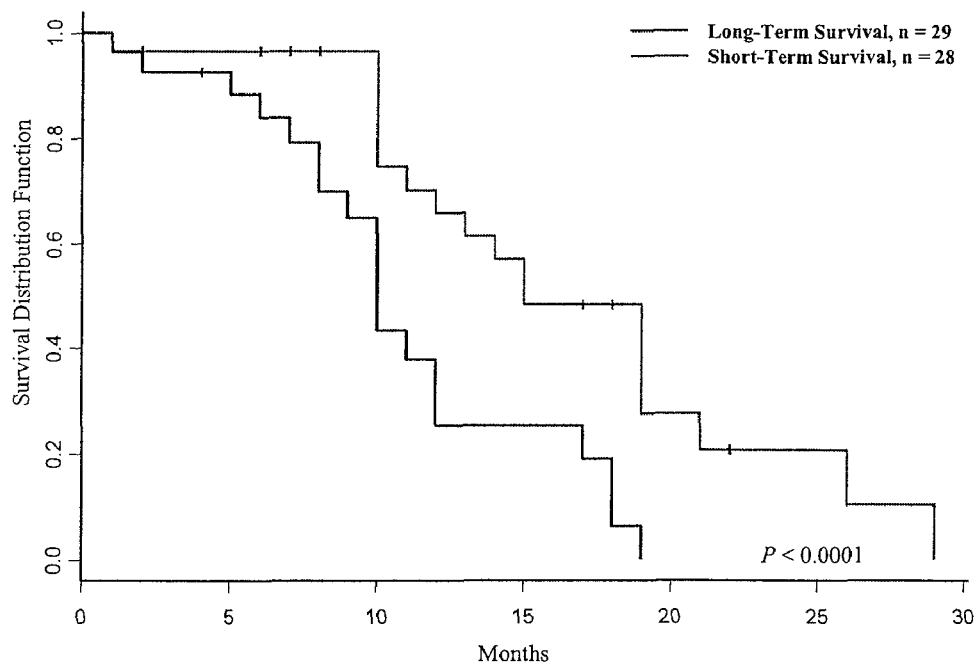
FIG. 4A-B

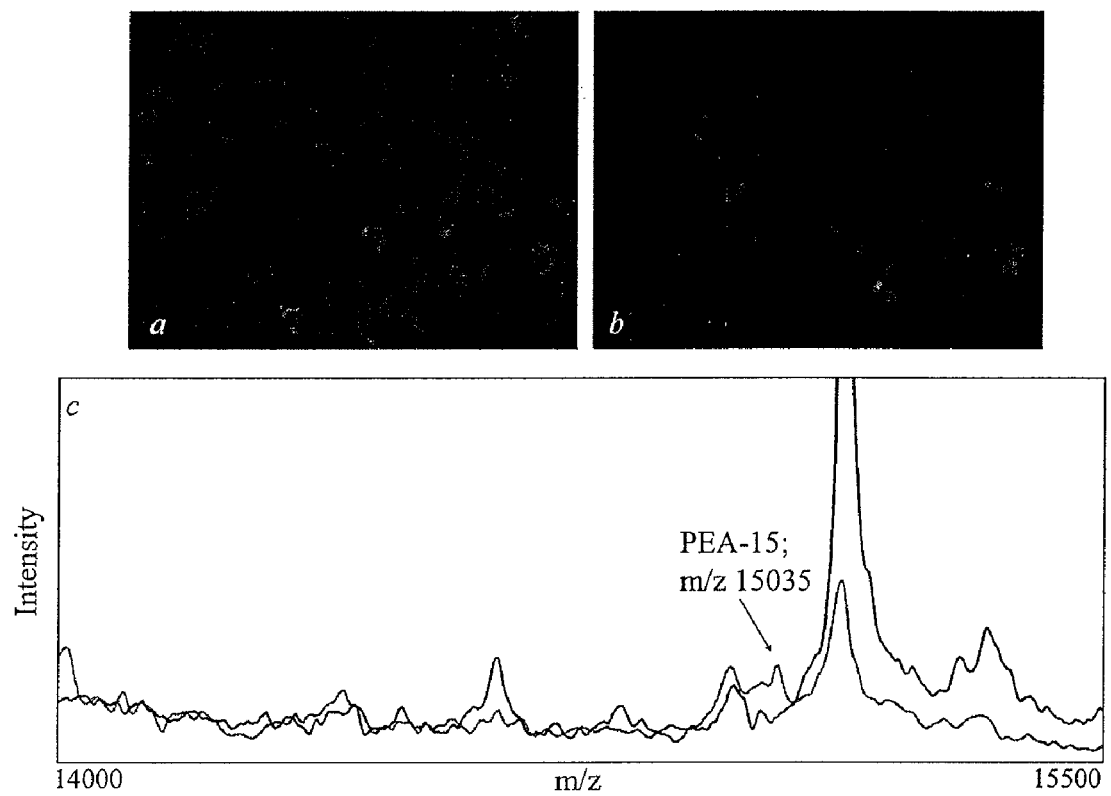
FIG. 5A-C

DIAGNOSING AND GRADING GLIOMAS USING A PROTEOMICS APPROACH

This application claims benefit of priority to U.S. Provisional Application Ser. No. 60/697,083, filed July 7, 2005, the entire contents of which are hereby incorporated by reference.

The government owns rights in the invention pursuant to funding from the NIH/NIGMS (GM 58008) and NIH/NCI/NIDA (CA 86243).

BACKGROUND OF THE INVENTION

1. Field of the Invention

The present invention relates generally to the fields of protein biology and oncology. More particularly, it concerns the classification of gliomas based on the expression of various proteins identified as relevant to various glioma states.

2. Description of Related Art

Gliomas are complex cancers with different growth characteristics and involves different types of cells. Because the original clone of tumor cells may exist at any stage during the cell differentiation, the boundaries between cell lineages can be blurred. The current morphologically-based tumor classifications often mix cell lineage features with tumor growth characteristics. The results are subjective and there can be disagreements among physicians as to what kind of tumor cell is involved. To date, a successful application of gene-based classification has not been applied to gliomas.

Molecular biology provides the potential for an improved method of tumor cell classification. This is based on the premise that all cell phenotypes have their origin in genetics. Thus, the rationale is that a detailed examination of gene expression will be the most accurate representation of a cell's character. Recent successes in the subclassification of neoplasms within a disease group using gene expression profiles provide support for such a belief (Golub et al., 1999; Alizadeh et al., 2000; Bittner et al., 2000).

Thus, the issue is how to best identify the "strong" feature genes that are closely linked to specific phenotypes from among the thousands of genes in gene expression profiles, and whether this information really aids classification of tumors more. There are many technical challenges in the path to accomplishing the task of finding the key links. Algorithms can assist in the identification of robust classifiers from very limited data sets. Three criteria have to be met: (a) given a set of variables, a classifier from the sample data should provide good classification over the general population; (b) the analysis should be able to estimate the error of a designed classifier when data are limited; and (c) given a large set of potential variables, the analysis should be able to select a set of variables as inputs to the classifier from the large number of expression level determinations provided by microarrays.

However, a major roadblock is the small sample size issue inherent to microarray-based classification efforts (Dougherty, 2001). Contributing to this are the limited numbers of human tissues for study and the cost of such gene expression profiling projects. Because classifiers are designed from observed expression vectors that have randomness arising from both biologic and experimental variability, the design, performance evaluation, and application of classifiers must take this randomness into account, especially when the number of samples (tissue specimens) is small, which is the case in most human tissue-based microarray studies.

SUMMARY OF THE INVENTION

Thus, in accordance with the present invention, there is provided a method of diagnosing or grading a glioma comprising (a) subjecting a tissue to mass spectrometry; (b) obtaining a mass spectrometric protein profile from the tissue; (c) comparing the mass spectrometric protein profile to a known profile; and (d) diagnosing or grading the tissue based on the similarities and differences between the mass spectrometric protein profile and the known profile. The mass spectrometry may be secondary ion mass spectrometry, laser desorption mass spectrometry, matrix assisted laser desorption mass spectrometry, or electrospray mass spectrometry. The method may further comprise obtaining the tissue from a patient, and may further comprise making a treatment decision for a patient from which the tissue was obtained.

The diagnosis may comprise distinguishing non-tumor from grade I, grade II, grade III or grade IV glioma; distinguishing grade I from grade II, grade III or grade IV glioma; distinguishing grade II from grade I, grade III or grade IV glioma; distinguishing grade III from grade I, grade II or grade IV glioma; or distinguishing grade IV from grade I, grade II, or grade III. The method may further comprise assessing one or more patient variables, such as age, gender, extent of tumor resection, use of pre-surgery chemotherapy, or use of pre-surgery radiotherapy. The known profile may be is a known glioma profile and/or a normal tissue profile. The method may further comprising performing a mass spectrometric analysis of a known glioma tissue and/or of a known normal tissue.

The method may further comprise performing histologic analysis on the tissue. The method may further comprise making a prediction of patient survival based on the grading. The method may further comprise making a prediction of drug efficacy based on the grading. The method may further comprising making a decision on drug dosing based on the grading. The method may further comprise making a prediction of patient survival based on the grading.

In another embodiment, there is provided a method of diagnosing or grading a glioma comprising (a) assessing glioma tissue for expression of one or more of calcyclin, dynein light chain 2, calpactin I light chain, astrocytic phosphoprotein PEA-15, fatty acid binding protein 5 and tubulin-specific chaperone A; (b) comparing the expression to a known tissue; and (c) grading the glioma based on the similarities and differences between the expression in the glioma and the known tissue. Assessing may comprise immunodetection, 2-D gel electrophoresis, or mass spectrometry, the mass spectrometry including secondary ion mass spectrometry, laser desorption mass spectrometry, matrix assisted laser desorption mass spectrometry, or electrospray mass spectrometry.

The method may further comprise obtaining the glioma tissue from a patient. The method may also further comprise making a treatment decision for a patient from which the glioma tissue was obtained, such as a decision involving predicting drug efficacy and or drug dosing. The diagnosis may comprise distinguishing non-tumor from grade I, grade II, grade III or grade IV glioma; distinguishing grade I from grade II, grade III or grade IV glioma; distinguishing grade II from grade I, grade III or grade IV glioma; distinguishing grade III from grade I, grade II or grade IV glioma; or distinguishing grade IV from grade I, grade II, or grade III.

The method may further comprise assessing one or more patient variables, such as age, gender, extent of tumor resection, use of pre-surgery chemotherapy, or use of pre-surgery radiotherapy. The known tissue may be a known glioma tissue, and the method may also further comprise assessing the known glioma tissue for expression of one or more of calcyclin, dynein light chain 2, calpactin I light chain, astrocytic phosphoprotein PEA-15, fatty acid binding protein 5 and tubulin-specific chaperone A. The known tissue may also be a known normal tissue, and the method may also comprise assessing the known normal tissue for expression of one or more of calcyclin, dynein light chain 2, calpactin I light chain, astrocytic phosphoprotein PEA-15, fatty acid binding protein 5 and tubulin-specific chaperone A. The method may further comprise performing histologic analysis on the tissue. The method may further comprise making a prediction of patient survival based on the grading.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-C: Hierarchical cluster analysis of normal brain and tumor tissues. (FIG. 3A) NT vs. T, (FIG. 3B) NT vs. $T_{IV}$ and (FIG. 3C) $T_{II}$ vs. $T_{IV}$ tissues in the training cohort were clustered according to the protein expression patterns determined by WFCCM analysis. Clustering was based on 28, 41, and 17 differentially-expressed protein signals, respectively. Each row represents an individual protein signal, characterized by a unique protein ID number (shown on the right), and each column represents an individual patient tissue sample. The dendrogram at the top clusters tissue samples based on similarity in protein expression profiles. Protein signal expression is characterized by cell color. Black reflects signal absence while red reflects signal presence; increasing signal intensity is denoted by an increasing red pixel scale. N=non-tumor, $T_{II}$=grade II tumor and $T_{IV}$=grade IV tumor.

FIGS. 4A-B: Kaplan-Meier survival curves and corresponding discriminatory mass signals for patient groups with a short-term or long-term prognosis according to MS proteomic patterns. Analyses were performed based on patient survival trends for (FIG. 4A) all glioma patients from the time of initial pathological diagnosis using 24 protein signals and (FIG. 4B) patients with grade IV glioblastoma from the time of GBM presentation using 2 protein signals.

FIGS. 5A-C: Immunohistochemical staining for PEA-15 validates biomarker identification. Two human glioma samples, a grade II astrocytoma and a grade IV glioblastoma multiforme were sectioned and analyzed to correlate MALDI MS protein profiling with PEA-15 immunohistochemical staining. Fluorescent immunohistochemical images collected from a (FIG. 5A) grade II astrocytoma and (FIG. 5B) grade IV glioblastoma after staining for PEA-15 are presented. Mass spectrometric profiles collected by direct-tissue MALDI MS analysis of serial glioma tissue sections are also displayed (FIG. 5C); the protein profiles from the grade II glioma (red trace) and the grade IV glioma (blue trace) are presented. The intensity of m/z signal 15035, identified in glioma cell lines as PEA-15, is increased in the MS profiles obtained from grade II as compared to grade IV gliomas. Images from serial tissue sections, stained with anti-PEA-15, corroborate this by demonstrating a stronger PEA-15 staining pattern in the grade II tumor specimen as compared to the grade IV sample.

DESCRIPTION OF ILLUSTRATIVE EMBODIMENTS

Figure 1:
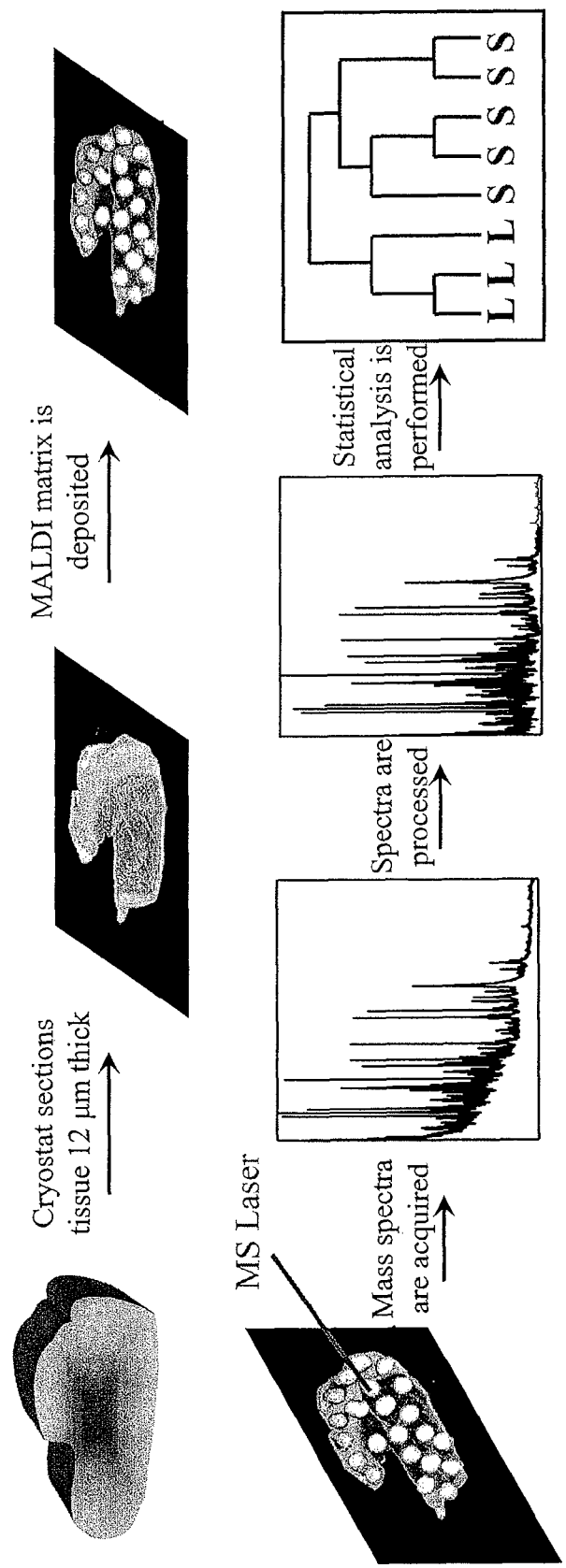
FIG. 1: Schematic of method. Protein profiles were collected directly from tissue sections and analyzed using classification programs for prognostic specific patterns. Tissue sections from tumor samples are collected and thawed onto MALDI target plates. Subsequent sections are collected for histological staining and analysis. Multiple matrix droplets are deposited on each section and each droplet region is analyzed by MALDI MS. Collected spectra are processed and the resulting peak lists are used in a classification analysis.

Gliomas are the most common malignant primary brain tumors. These tumors are derived from neuroepithelial cells and can be divided into two principal lineages: astrocytomas and oligodendrogliomas. Current glioma classification schemes are based on morphologic feature assessment and remain highly subjective and problematic. Diagnoses are often dependent on the relative weighting of specific morphologic features by individual pathologists.

The present inventor used direct tissue profiling by MALDI MS to analyze the protein patterns within human gliomas and correlate these patterns to tumor classification and patient survival. These data can be used to distinguish tumor tissue from non-tumor brain tissue, define protein profiles specific to tumor grade, and identify differential patient survival patterns based on protein expression patterns.

Since the accepted standard for glioma classification is histopathological grading, the inventor initially sought to validate the MS approach by identifying grade-specific biomarkers that correlated to histopathologically-determined classifications. Tumors were sub-classified by two neuropathologists, blinded to the original diagnosis, and analyzed by MALDI MS without knowledge of the original classification. Only samples with coincident clinical diagnoses were included in the analysis. Based on two independent classification approaches, WFCCM and SDA, MALDI MS provided specific proteomic patterns that classified glial tumors and non-tumor brain tissue with high accuracy and precision. Proteomic profiles were used to discriminate between normal brain tissue and gliomas >92% of the time, with individual classification accuracies between normal tissues and individual grades ranging from 92-100%. In addition, MALDI MS patterns were used to distinguished glioma grades with high accuracy, ranging from 76-97%. The most difficult distinction was between WHO grade II and grade III tumors, which mimics the clinical situation. Statistical analysis identified over 100 potential, tumor-specific biomarkers. Validation of MS-based tumor classification using two different statistical techniques highlights the power of protein profiling for tissue characterization, independent of the analysis approach.

WFCCM was also applied to identify MS-derived protein patterns that correlate to patient survival trends for all glioma patients and for a subgroup of patients with histologically-confirmed GBM. For all patients, standard treatment regimens were followed including surgical tumor resection plus adjuvant radiotherapy and chemotherapy, as clinically-indicated and tolerated. The inventor demonstrated that a relatively small number of proteins can be used to distinguish between short-term and long-term survival patients within the glioma patient population as a whole (P<0.0001). While these results are in line with previous clinical and pathological studies, demonstrating that the WHO grading system possesses discriminating predictive power, the protein pattern was an independent indicator of patient survival.

In addition, MALDI MS protein profiling was used to analyze a large group of patients with the most malignant form of glioma, GBM, and found that the MS pattern from two m/z signals could further stratify patients into a short-term and long-term survival group (P<0.0001). For both analyses, the MALDI MS profile was the strongest determinant of survival in both univariate and multi-variate analyses, stronger than most previously-identified predictive variables such as age, extent of resection, tumor grade, and use of adjuvant therapy. As expected, for the full glioma population some overlap exists between grade specific biomarkers and the survival markers. Of the 24 discriminatory patient survival biomarkers for the entire glioma population, 17 were unique to the survival stratification. On the other hand, analysis of the GBM population determined two unique markers that segregated the STS and LTS patients. These results suggest a novel approach to tissue classification based not on histopathological features requiring visual analysis but on a molecular analysis of the protein patterns specific to the tissue sample.

Based on statistical analysis, a number of discriminatory proteins were identified including calcyclin, dynein light chain 2, calpactin I light chain, astrocytic phosphoprotein PEA-15, fatty acid binding protein 5 and tubulin-specific chaperone A. The mass spectrometric signals from these proteins serve to discriminate gliomas from normal brain tissue and tumors of differing grade from one another; calcyclin and dynein light chain 2 also discriminated between glioma survival subgroups. These proteins are thought to be involved in several aspects of tumorigenesis. Calcyclin (S100A6), which plays a potential role in cell cycle progression and cell differentiation (Toini et al., 1995), is overexpressed in many tumors, especially at the margins of invasive cancers (Camby et al., 1999; Komatsu et al., 2002; Bronckart et al., 2001; Stulik et al., 2000). Dynein light chain 2, a subunit of the microtubule-associated dynein motor complex, binds and sequesters Bim, a proapoptotic protein, to negatively regulate its apoptotic function (Puthalakath et al., 1999). Calpactin I light chain (p11, S100A10) is expressed in many cancer cell lines (Zhi et al., 2003; El-Rifai et al., 2002) and is thought to bind and stimulate plasminogen conversion to plasmin, a cell surface proteinase involved in tumor cell invasion and metastasis (Zhang et al., 2004). PEA-15, an apoptosis inhibitor involved in several cell growth pathways (Condorelli et al., 1999; Ramos et al., 2000), is overexpressed in several tumor cell lines including breast, larynx, cervix and skin (Ramos et al., 2000; Condorelli et al., 1998) while studies have suggested overexpression of the fatty acid binding protein 5 gene in prostate cancer tissue and cell lines (Vaarala et al., 2000). Tubulin specific chaperone A is a cofactor required for proper β-tubulin folding (Melki et al., 1996).

Identification of these proteins was performed in both a human glioblastoma cell line as well as a human glioblastoma tissue sample. These studies demonstrated that, while cell lines are not ideal sources for protein identification, due to potential posttranslational modifications and genomic mutations specific to the cell lines, a positive correlation between the proteins identified from a cell line versus a tissue sample can exist. The identification of proteins from cell lines followed by further characterization of these proteins using traditional immunohistochemistry methods in intact tissues should serve as a valuable tool for protein identification and biomarker validation when resources are limited.

This analysis has several potential limitations. A rank cut-off was used in WFCCM to determine the number of protein signals used in each classification. Therefore, the number of peaks reported is based not on the smallest or largest number of signals that could discriminate the classes, but rather on an intermediate number based on statistical evidence. It may be possible to achieve a similar classification rate using a different subset of peaks. While a variety of variables could lead to the misclassified samples, potential limitations include the diffuse cellular nature of the tumors as well as histopathological inaccuracy. Furthermore, the tumors were not analyzed for genetic alterations suspected of playing a role in gliomagenesis, which may have prognostic significance, nor did we control for histological homogeneity or require a specific treatment regimen. While it may have been useful to focus this study on a homogeneous study population, the mixed nature of the tumors more faithfully corresponds to the clinical situation.

In summary, MALDI MS protein profiling has been used to determine protein expression patterns that distinguish primary gliomas from normal brain tissue, and one grade of gliomas from another, with high sensitivity and specificity. In addition, the inventor has demonstrated that a small subset of protein signals can be used to predict survival of glioma patients, as well as to identify differential survival patterns within a more homogenous population of GBM patients. Since MALDI MS technology is capable of analyzing numerous samples, with analysis times of approximately five minutes per sample, this technology is amenable to high-throughput tissue screening in a clinical setting.

I. GLIOMAS

Gliomas are a diverse group of brain tumors that arise from the normal "glial" cells of the brain. The most important determinant of survival for gliomas is the "grade" of the glioma. The low-grade gliomas have a protracted natural history, while the high grade gliomas (anaplastic astrocytoma and glioblastoma multiforme) are much more difficult to successfully treat. The gliomas have specific signs and symptoms that are primarily related to the location of the glioma.

The temporal lobe gliomas, for example, may cause epilepsy, difficulty with speech or loss of memory. The frontal lobe gliomas may cause behavioral changes, weakness of the arms or legs or difficulty with speech. The occipital gliomas may cause loss of vision. The parietal gliomas may cause loss of spatial orientation, diminished sensation on the opposite side of the body, or inability to recognize once familiar objects or persons.

Grading according to degree of malignancy was first proposed in 1949. In this classification, astrocytomas and glioblastomas represent different grades of malignancy of the same tumor. Grade I tumors, typically slow growing, are characterized by most cells having normal characteristics, and few mitotic features. Endothelial proliferation is absent. Grade II tumors, previously designated "astroblastomas," are characterized by an increased number of cells with polymorphic nuclei in mitoses. There is no clear line of demarcation from normal tissue. Grade III tumors represent anaplastic astrocytomas and Grade IV tumors represent the typical glioblastoma multiforme, characterized by cellular pleomorphism, vascular proliferation, mitoses, and multinucleated giant cells.

Surgery. The role of surgical resection in the treatment of malignant gliomas remains controversial even after 75 years of experience with primary malignant gliomas. Surgery permits a pathologic diagnosis to be established while the patient is still alive. However, many physicians argue that current radiologic imaging methods, including computed tomography (CT) and magnetic resonance imaging (MRI), permit a malignant brain tumor to be diagnosed without the necessity for attempted tumor resection and, thus, avoid the risks of surgery.

There is evidence that surgical reduction of tumor to very small residual amounts can prolong survival and permit patients to return to active lives. However, retrospective studies are subject to the criticism that the extent of attempted resection depends on the condition of the patient at the time of surgery (age, tumor location, clinical state), and that favorable conditions usually lead the surgeon to attempt a greater resection. Therefore, in such studies, it is not clear that the extent of surgery is as important to survival as are the more favorable prognostic variables. Nevertheless, these results support the surgical removal of the largest possible tumor volume that can be done safely. Patients are frequently able to return to a full, active life without the need for large doses of corticosteroids to ameliorate incapacitating symptoms.

Radiation. The proper portals and doses of radiation for brain tumors have changed with the advent of better imaging techniques. It has been reported in controlled studies that postoperative whole-brain radiation therapy increases patient survival over surgery alone. Other data showed that patients receiving 5,500 to 6,000 cGy of radiation live significantly longer than those receiving 5,000 cGy.

Prolonged survival has been reported in patients with recurrent malignant gliomas who were treated with temporarily implanted $I^{125}$ sources. A phase III trial randomized newly diagnosed patients to receive either (a) postoperative temporary $I^{125}$ seed implantation in the residual tumor bed, followed by standard external-beam radiotherapy plus IV BCNU; or (b) external radiotherapy plus BCNU, without seed implantation. Preliminary review of the results demonstrated that patients who received $I^{125}$ seeds lived longer than those who did not receive seeds, although the difference did not quite reach statistical significance. The study suggests but does not prove that brachytherapy extends survival beyond that achievable with external radiotherapy alone.

Radiosurgery. Radiosurgery, either by gamma knife or linear accelerator, has been shown to be effective in the treatment of arteriovenous malformations, small primary and metastatic brain tumors, and benign brain tumors, such as meningiomas and acoustic neuromas. Its investigational use in the treatment of gliomas has been addressed in several reports. In one trial, 37 patients received radiosurgery (1,000 to 2,000 cGy) to residual contrast-enhancing tumor after treatment with conventional external-beam radiation therapy. Local recurrence still occurred, but overall survival time may have been prolonged. Of the 37 patients, 7 (19%) required reoperation at a median time of 5 months after radiosurgery to remove necrotic tumor.

A major problem with radiosurgery (as with brachytherapy) is bias in the selection of patients for treatment. However, radiosurgery may be of benefit in a small group of good-prognosis patients with small tumors.

Chemotherapy. In 1983, it was reported that surgery plus radiation therapy and BCNU chemotherapy significantly adds to the survival of patients with malignant glioma, as compared with surgery plus radiation therapy without chemotherapy. High-dose methylprednisolone does not prolong survival. Both procarbazine and streptozotocin have demonstrated effectiveness similar to that of BCNU. BCNU alone is as effective as BCNU followed by procarbazine, or BCNU plus hydroxyurea followed by procarbazine plus teniposide. Methotrexate also has been reported to be effective in treating gliomas.

Intra-arterial BCNU is no more effective than intravenous BCNU and substantially more toxic. Serious toxicity induced by intra-arterial BCNU included irreversible encephalopathy and/or visual loss ipsilateral to the infused carotid artery. In the same study, fluorouracil did not influence survival. Neuropathologically, intra-arterial BCNU produced white matter necrosis. Intra-arterial cisplatinum is safer than BCNU administered by the same route but is no more effective than another nitrosourea, PCNU.

Over the past several years, there has been increasing interest in the use of targeted interstitial drug delivery using biodegradable microspheres and wafers. In a multicenter controlled trial, 222 patients with recurrent malignant gliomas who required reoperation were randomly assigned to receive surgically implanted biodegradable polymer discs containing 3.85% of BCNU or discs containing placebo. Median survival of the 110 patients who received BCNU polymers was significantly longer than that of the 112 patients who received placebo polymers (31 versus 23 weeks).

In addition to these controlled survival-based clinical trials, a large number of agents have also been tested in response-based studies in glioma patients. To date, however, no drug has been found to be more effective than the nitrosoureas. The combination of procarbazine, CCNU, and vincristine (PCV) has become a popular chemotherapeutic regimen for malignant glioma, and may be more effective than BCNU alone.

1. Glioblastoma Multiforme

Glioma-glioblastoma multiforme (GBM), referred to a Grade IV glioma, is the most malignant of the neuroepithelial neoplasms, characterized by cellular pleomorphism, numerous mitotic figures, and often multinucleated giant cell. Proliferation of the vascular endothelium is seen as well as areas of necrosis with circumjacent pseudopalisading of the neoplastic cells. It can appear as either a well-circumscribed globular mass or a more diffuse mass lesion. The cut surface reveals necrosis, fatty degeneration, and hemorrhage. Hemorrhages have been found in 40%, with necrosis in up to 52% of the cases. The tumor is usually solid, although cysts may be present. Rarely the tumor consists of a solitary cyst and mural nodule.

Glioblastoma multiforme constitutes approximately 7% of childhood intracranial neoplasms. The overall male to female ratio in children is 3:2. In adults, glioblastomas are noted most frequently in the frontal lobe with the temporal lobe second in frequency. Childhood glioblastomas of the cerebral hemispheres are also located most often in the frontal lobe; with the second most frequent site being the parietal lobe. Primary glioblastoma of the spinal cord in childhood is rare.

Glioblastoma multiforme in children appears to have two characteristic courses, each of which is related to the location of the tumor. Glioblastomas of the brainstem, a more primitive part of the central nervous system, occur at a younger age and have a shorter mean survival relative to those of the cerebral hemispheres. Glioblastoma multiforme of the cerebral hemisphere, a more highly developed part of the central nervous system, is characterized by onset in older children (13 years) and by a longer mean survival.

Headache is the most common complaint and papilledema the most common physical finding in children with hemispheric glioblastoma. Seizures are noted in up to one third of the children. Survival rates in patients with glioblastoma multiforme is uniformly poor. In studies of children treated with surgery and intracranial radiation, only one third of the children are alive one year after diagnosis. Survival of children with glioblastoma multiforme of either of the cerebral hemispheres or the brainstem has significantly increased since the advent of dexamethasone therapy. Presently therapy consists of surgery plus combination chemotherapy.

In summary it can be said that glioblastoma multiforme behaves similarly in both children and adults. The course of intracranial glioblastomas in children is more rapidly fatal than that of other similarly situated gliomas in childhood. While the overall survival rate is very poor in patients with a glioblastoma multiforme, intensive chemotherapy with surgical resection does offer some hope in increasing survival time among children.

2. Astrocytoma

Astrocytomas are tumors that arise from brain cells called astrocytes. Gliomas originate from glial cells, most often astrocytes. Sometimes the terms "astrocytoma" and "glioma" are used interchangeably. Astrocytomas are of two main types—high-grade and low-grade. High-grade tumors grow rapidly and can easily spread through the brain. Low-grade astrocytomas are usually localized and grow slowly over a long period of time. High-grade tumors are much more aggressive and require very intense therapy. The majority of astrocytic tumors in children are low-grade, whereas the majority in adults are high-grade. These tumors can occur anywhere in the brain and spinal cord. Common sites in children are the cerebellum (the area just above the back of the neck), cerebral hemispheres (the top part of the brain), and the thalamus or hypothalamus (located in the center of the brain).

Astrocytomas account for the majority of pediatric brain tumors. About 700 children are diagnosed with low-grade astrocytomas each year. In children, about 90 percent of astrocytomas are low-grade; only about 10 percent are high-grade.

Clinical features and symptoms depend on the location of the tumor and the child's age. The most common location is the cerebellum. Patients with cerebellar tumors have symptoms that include headache, vomiting and unsteadiness in walking. Tumors in the cerebral hemispheres commonly present with seizures: occasionally there is weakness of the arms and legs. Tumors in the hypothalamus often present with visual problems, while thalamic tumors cause headaches and arm or leg weakness.

Complete surgical removal of the tumor (resection) is the best option for tumors in areas where this can be done without damaging the normal, surrounding brain. For low-grade astrocytomas that are completely removed, further therapy is usually not needed. If the surgeon cannot completely remove the tumor, chemotherapy or radiation therapy may be given. The choice of treatments depends on the age of the patient, tumor location; some patients may even be followed without treatment. Radiation therapy is used for older children and those whose tumors keep growing despite chemotherapy. About 90 percent of children with low-grade astrocytomas are alive five years from diagnosis.

High-grade astrocytomas can rarely be removed totally because they often affect large areas of the brain by the time symptoms are obvious. All patients with high-grade astrocytomas usually recieve chemotherapy regardless of age. Most, except the very youngest, also receive radiation therapy. Currently, the prognosis is poor in the group of patients. The subset of patients who have high-grade tumors that can be removed may have survival rates of 35 to 40 percent after postsurgical irradiation with chemotherapy. The survival of other patients is very poor.

Research efforts for the low-grade astrocytomas focus on developing chemotherapy regimens that control tumor growth with fewer side effects on other organs of the body. Because these tumors grow slowly, the strategy is to give less intensive chemotherapy over longer periods of time. For older children and those whose tumors progress despite chemotherapy, new radiation techniques are under study to deliver more localized therapy with minimal effects on the normal brain.

For high-grade tumors, new approaches include use of new chemotherapy drugs, and the potential option of high doses of chemotherapy. Investigational new approaches, including new chemotherapy drugs and gene therapy to help protect the bone marrow from the side effects so that more intensive chemotherapy can be given are in various stages of development.

3. Oligodendroglioma and Anaplastic Oliogodendroglioma

Oligodendrogliomas are believed to be tumors of cells called oligodendrocytes that have a role in the structure and function of the brain. However, the origins of these tumor cells has been questioned. Oligodendrogliomas are classified as low grade oligodendroglioma (less aggressive) and anaplastic oligodendroglioma (more aggressive). More common that pure oligodendrogliomas are low grade and anaplastic tumors that are a mixture of astrocytoma and oligodendroglioma ("oligoastrocytomas").

The initial treatment of low grade oligodendroglioma and oligoastrocytoma consists of maximal surgery. The role of radiation therapy has been disputed, but younger people with minimal residual disease after surgery may have radiation therapy deferred as long as there is adequate monitoring of the tumor by MRI or CT scanning.

Anaplastic oligodendrogliomas and mixed oligoastrocytomas are more sensitive to chemotherapy than astrocytomas. A high rate of response to the use of PCV (procarbazine, CCNU, vincristine) chemotherapy has made the use of chemotherapy prior to radiation therapy the standard of care for these tumors. The actual effectiveness of this treatment regimen is currently being investigated in a large multinational trial.

Additionally, low grade oligodendrogliomas are also sensitive to chemotherapy, and PCV can be used when low grade tumors begin to grow despite prior radiation therapy.

II. GLIOMA-RELATED GENES AND THEIR CLASSIFICATION

As discussed above, the present invention provides a protein-based classification of gliomas. This classification is based on the identification of six particular proteins, the expression of which correlates with the various glioma disease states. Using information derived from these six targets, one can grade a glioma. The six proteins are calcyclin, dynein light chain 2, calpactin I light chain, astrocytic phosphoprotein PEA-15, fatty acid binding protein 5 and tubulin-specific chaperone A.

1. Calcyclin

A member of the S100 family of calcium binding proteins, calcyclin in is A prolactin receptor-associated protein, one of a family of small (around 10 kD) calcium-binding proteins containing the EF-hand motif, originally isolated from Erlich ascites tumour cells, but human and rat forms now identified. It is regulated through the cell cycle and binds to annexin II (p36) and to glyceraldehyde-3-phosphate dehydrogenase. In situ hybridization shows that, in mouse, calcyclin transcripts are restricted to specific cell types within a limited number of organs. High levels of expression in the epithelia lining the gastrointestinal, respiratory and urinary tracts, and specific localization of the transcripts to the goblet cells in the small intestine, lead to a suggestion for a role in the process of mucus secretion. In addition, calcyclin expression is detected in mouse corpus luteum, placenta and nerves within the gut wall, which are all sites of regulated exocytosis.

2. Calpactin I Light Chain

Calpactins are a family of related $Ca^{2+}$-regulated cytoskeletal proteins and, like calcyclin are a members of the S100 family of proteins containing EF-hand calcium-binding motifs. Comparison of the tissue distribution of calpactin I heavy and light chains by Western blots revealed that these subunits are coordinately expressed. Both soluble and cytoskeletal forms of the heavy chain of calpactin I were detected in human fibroblasts, whereas only a soluble pool of calpactin II was found. These two forms of the calpactin I heavy chain differed both in their state of association with the light chain and in their rate of turnover. Both the soluble pool of the calpactin I heavy chain and calpactin II turned over three to four times faster than the cytoskeletal pool of heavy and light chains. Immunofluorescence microscopy revealed that the calpactin I light chain was present exclusively in the cytoskeleton, whereas the calpactin I heavy chain distribution was more diffuse. Calpactin I light chain is also known as a ligand for annexin II. This protein is designated as p11, and is coded by a human gene designated as CPL11.

3. Astrocytic Phosphoprotein PEA-15

Astrocytic phosphoprotein PEA-15 inhibits both fas- and tnfrsf1a-mediated caspase-8 activity and apoptosis. It also regulates glucose transport by controlling both the content of s1c2a1 glucose transporters on the plasma membrane, and the insulin-dependent trafficking of s1c2a4 from the cell interior to the surface. It is associated with microtubules, interacts with casp8/flice and fadd, and contains 1 death effector (ded) domain.

Phosphorylated by protein kinase c and calcium-calmodulin-dependent protein kinase, these phosphorylation events are modulated by neurotransmitters or hormones. It is ubiquitously expressed, and is most abundant in tissues such as heart, brain, muscle and adipose tissue which utilize glucose as an energy source. Lower expression is observed in glucose-producing tissues, and higher levels of expression are found in tissues from individuals with type 2 diabetes than in controls.

4. Tubulin Specific Chaperone A

Cofactor A is one of four proteins (cofactors A, D, E, and C) involved in the pathway leading to correctly folded β-tubulin from folding intermediates. Cofactors A and D are believed to play a role in capturing and stabilizing β-tubulin intermediates in a quasi-native confirmation. Cofactor E binds to the cofactor D/β-tubulin complex; interaction with cofactor C then causes the release of β-tubulin polypeptides that are committed to the native state.

By immunofluorescence microscopy analysis, Martin et al (2000) demonstrated that overexpression of TBCD correlates with microtubule depolymerization and a progressive loss of microtubules, leading to a rapid drop in levels of α-tubulin but not β-tubulin. The results showed that TBCD modulates microtubule dynmaics by capturing GTP-bound β-tubulin. The interactions did not lead to apoptosis.

5. Dynein Light Chain 2

DLC2 encodes a novel Rho-family protease with a RhoGAP domain, a SAM (sterile a motif) domain related to p73/p63, and a lipid-binding StAR-related lipid transfer (START) domain. It is found at at 13q12.3. Biochemical analysis indicates that DLC2 protein has GAP activity specific for small GTPases RhoA and Cdc42. DLC2 is homologous to DLC1, a previously identified tumor suppressor gene at 8p22-p21.3 frequently deleted in HCC. Remarkably, mutational analysis of DLC1 and DLC2 indicates that a single surface residue (residue 41) determines the specific localization of DLCs with their respective motor complexes. In vivo, DLC2 is found exclusively as a component of the myosin V motor complex and Bmf binds DLC2 selectively.

6. Fatty Acid Binding Protein 5

Adipocyte fatty acid binding protein FABP5 is a 15 kD member of the intracellular fatty acid binding protein (FABP) family, which is known for the ability to bind fatty acids and related compounds (bile acids or retinoids) in an internal cavity. The fatty acid binding proteins aP2 (fatty acid binding protein [FABP]-4) and mall (FABP5) are closely related and both are expressed in adipocytes. Absence of FABP5/mal1 results in increased systemic insulin sensitivity in two models of obesity and insulin resistance. Adipocytes isolated from mal1-deficient mice also exhibited enhanced insulin-stimulated glucose transport capacity. In contrast, mice expressing high levels of mall in adipose tissue display reduced systemic insulin sensitivity

III. PROGNOSTIC DETERMINATION IN GLIOMA

In addition to the glioma classification methods described above, the present invention also provides for making predictions on the clinical prospects of a glioma patient. Again, the inventors have used statistical analysis of data to select the following set of proteins that are differentially regulated in various forms of glioma and thus permit the accurate classification of each type of glioma: calcyclin, calpactin I light chain, astrocytic phosphoprotein PEA-15 and tubulin-specific chaperone A. Using information derived from these targets, one can predict whether a glioma patient will be a long term survivor or not.

IV. PROTEIN-BASED DETECTION—IMMUNODETECTION

Thus, in accordance with the present invention, methods are provided for the assaying of protein expression in patients suffering from gliomas. As discussed above, the principle applications of this assay are to: (a) determine what grade of glioma a given patient suffers from; and (b) determine the likelihood and extent of patient survival. In each of these assays, the expression of a particular set of target proteins, set forth in the preceding sections, will be measured.

There are a variety of methods that can be used to assess protein expression. One such approach is to perform protein identification with the use of antibodies. As used herein, the term "antibody" is intended to refer broadly to any immunologic binding agent such as IgG, IgM, IgA, IgD and IgE.

Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies, both polyclonal and monoclonal, are also well known in the art (See, e.g., Antibodies: A Laboratory Manual, Cold Spring Harbor Laboratory, 1988; incorporated herein by reference). In particular, antibodies to calcyclin, calpactin I light chain, astrocytic phosphoprotein PEA-15 and tubulin-specific chaperone A are contemplated.

In accordance with the present invention, immunodetection methods are provided. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle & Ben-Zeev O, 1999; Gulbis & Galand, 1993; De Jager et al., 1993; and Nakamura et al., 1987, each incorporated herein by reference.

In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays are in essence binding assays. Certain immunoassays are the various types of enzyme linked immunosorbent assays (ELISAs) and radioimmunoassays (RIA) known in the art. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the invention. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has binding affinity for the first anti-ORF message and anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present invention is the use of immunohistochemistry. This approach uses antibodies to detect and quantify antigens in intact tissue samples. Generally, frozen-sections are prepared by rehydrating frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and cutting up to 50 serial permanent sections.

V. PROTEIN-BASED DETECTION—MASS SPECTROMETRY

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can generate mass spectrometry profiles that are useful for grading gliomas and predicting glioma patient survival, without regard for the identity of specific proteins. Alternatively, given the established links with calcyclin, calpactin I light chain, astrocytic phosphoprotein PEA-15 and tubulin-specific chaperone A, mass spectrometry may be used to look for the levels of these proteins particularly.

1. ESI

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 µL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as a small highly electrically charged droplets and further undergoes desolvation and breakdown to form single or multicharged gas phase ions in the form of an ion beam. The ions are then collected by the grounded (or negatively charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

2. ESI/MS/MS

In ESI tandem mass spectroscopy (ESI/S/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

3. SIMS

Secondary ion mass spectroscopy, or SIMS, is an analytical method that uses ionized particles emitted from a surface for mass spectroscopy at a sensitivity of detection of a few parts per billion. The sample, surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

4. LD-MS and LDLPMS

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation require a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

5. MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

VI. NUCLEIC ACID DETECTION

In alternative embodiments for detecting protein expression, one may assay for gene transcription. For example, an indirect method for detecting protein expression is to detect mRNA transcripts from which the proteins are made. The following is a discussion of such methods, which are applicable particularly to calcyclin, calpactin I light chain, astrocytic phosphoprotein PEA-15 and tubulin-specific chaperone A in the context of the present invention.

1. Hybridization

There are a variety of ways by which one can assess gene expression. These methods either look at protein or at mRNA levels. Methods looking at mRNAs all fundamentally rely, at a basic level, on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Molecules having complementary sequences over contiguous stretches greater than 20 bases in length are generally preferred, to increase stability and selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Since many mRNAs are present in relatively low abundance, nucleic acid amplification greatly enhances the ability to assess expression. The general concept is that nucleic acids can be amplified using paired primers flanking the region of interest. The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to selected genes are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemilluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Whereas standard PCR usually uses one pair of primers to amplify a specific sequence, multiplex-PCR (MPCR) uses multiple pairs of primers to amplify many sequences simultaneously (Chamberlan et al., 1990). The presence of many PCR primers in a single tube could cause many problems, such as the increased formation of misprimed PCR products and "primer dimers", the amplification discrimination of longer DNA fragment and so on. Normally, MPCR buffers contain a Taq Polymerase additive, which decreases the competition among amplicons and the amplification discrimination of longer DNA fragment during MPCR. MPCR products can further be hybridized with gene-specific probe for verification. Theoretically, one should be able to use as many as primers as necessary. However, due to side effects (primer dimers, misprimed PCR products, etc.) caused during MPCR, there is a limit (less than 20) to the number of primers that can be used in a MPCR reaction. See also European Application No. 0 364 255 and Mueller and Wold (1989).

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Nucleic Acid Arrays

Microarrays comprise a plurality of polymeric molecules spatially distributed over, and stably associated with, the surface of a substantially planar substrate, e.g., biochips. Microarrays of polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e., target, such as polyA mRNA from a particular tissue type. Contact is carried out under hybridization conditions and unbound nucleic acid is then removed. The resultant pattern of hybridized nucleic acid provides information regarding the genetic profile of the sample tested. Methodologies of gene expression analysis on microarrays are capable of providing both qualitative and quantitative information.

A variety of different arrays which may be used are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single- or double-stranded, usually single-stranded, and may be PCR fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed, and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, S1 nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3' end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

VI. GENE THERAPY

In another embodiment, the present invention provides for the administration of a gene therapy vector encoding one or more genes identified as being downregulated in gliomas. Alternatively, for genes that are overexpressed in gliomas, the transgenes may provide for reduced expression of appropriate targets. Various aspects of gene delivery and expression are set forth below.

1. Therapeutic Transgenes

Thus, in accordance with the present invention, there are provided methods of treating cancer utilizing genes identified as being overexpressed or underexpressed in gliomas. By inhibiting or increasing the expression of various of these genes, therapeutic benefit may be provided to patients.

2. Antisense

The term "antisense" nucleic acid refers to oligo- and polynucleotides complementary to bases sequences of a target DNA or RNA. When introduced into a cell, antisense molecules hybridize to a target nucleic acid and interfere with its transcription, transport, processing, splicing or translation. Targeting double-stranded DNA leads to triple helix formation; targeting RNA will lead to double helix formation.

Antisense constructs may be designed to bind to the promoter or other control regions, exons, introns or even exon-intron boundaries of a gene. Antisense RNA constructs, or DNA encoding such antisense RNA's, may be employed to inhibit gene transcription or translation within a host cell. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine in the case of DNA (A:T), or uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" and "antisense sequences" mean nucleic acid sequences that are substantially complementary over their entire length and have very few base mismatches. For example, nucleic acid sequences of fifteen bases in length may be termed complementary when they have complementary nucleotides at thirteen or fourteen positions. Naturally, nucleic acid sequences with are "completely complementary" will be nucleic acid sequences which have perfect base pair matching with the target sequences, i.e., no mismatches. Other sequences with lower degrees of homology are contemplated. For example, an antisense construct with limited regions of high homology, but overall containing a lower degree (50% or less) total homology, may be used.

While all or part of the gene sequence may be employed in the context of antisense construction, statistically, any sequence of 17 bases long should occur only once in the human genome and, therefore, suffice to specify a unique target. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting a gene simply by testing the construct in vitro to determine whether the gene's function or expression is affected.

In certain embodiments, one may wish to employ antisense constructs which include other elements, for example, those which include C-5 propyne pyrimidines. Oligonucleotides which contain C-5 propyne analogs of uridine and cytidine have been shown to bind RNA with high affinity and to be potent inhibitors or gene expression. Wagner et al. (1993).

3. Ribozymes

The term "ribozyme" refers to an RNA-based enzyme capable of targeting and cleaving particular DNA and RNA sequences. Ribozymes can either be targeted directly to cells, in the form of RNA oligonucleotides incorporating ribozyme sequences, or introduced into the cell as an expression construct encoding the desired ribozymal RNA. Ribozymes may be used and applied in much the same way as described for antisense nucleic acids. Ribozyme sequences also may be modified in much the same way as described for antisense nucleic acids. For example, one could include modified bases or modified phosphate backbones to improve stability or function.

4. Single Chain Antibodies

Naturally-occurring antibodies (of isotype IgG) produced by B cells, consist of four polypeptide chains. Two heavy chains (composed of four immunoglobulin domains) and two light chains (made up of two immunoglobulin domains) are held together by disulphide bonds. The bulk of the antibody complex is made up of constant immunoglobulin domains. These have a conserved amino acid sequence, and exhibit low variability. Different classes of constant regions in the stem of the antibody generate different isotypes of antibody with differing properties. The recognition properties of the antibody are carried by the variable regions (VH and VL) at the ends of the arms. Each variable domain contains three hypervariable regions known as complementarity determining regions, or CDRs. The CDRs come together in the final tertiary structure to form an antigen binding pocket. The human genome contains multiple fragments encoding portions of the variable domains in regions of the immunoglobulin gene cluster known as V, D and J. During B cell development these regions undergo recombination to generate a broad diversity of antibody affinities. As these B cell populations mature in the presence of a target antigen, hypermutation of the variable region takes place, with the B cells producing the most active antibodies being selected for further expansion in a process known as affinity maturation.

A major breakthrough was the generation of monoclonal antibodies, pure populations of antibodies with the same affinity. This was achieved by fusing B cells taken from immunized animals with myeloma cells. This generates a population of immortal hybridomas, from which the required clones can be selected. Monoclonal antibodies are very important research tools, and have been used in some therapies. However, they are very expensive and difficult to produce, and if used in a therapeutic context, can elicit and immune response which will destroy the antibody. This can be reduced in part by humanizing the antibody by grafting the CDRs from the parent monoclonal into the backbone of a human IgG antibody. It may be better to deliver antibodies by gene therapy, as this would hopefully provide a constant localized supply of antibody following a single dose of vector. The problems of vector design and delivery are dealt with elsewhere, but antibodies in their native form, consisting of two different polypeptide chains which need to be generated in approximately equal amounts and assembled correctly are not good candidates for gene therapy. However, it is possible to create a single polypeptide which can retain the antigen binding properties of a monoclonal antibody.

The variable regions from the heavy and light chains (VH and VL) are both approximately 110 amino acids long. They can be linked by a 15 amino acid linker (e.g., (glycine$_4$serine)$_3$), which has sufficient flexibility to allow the two domains to assemble a functional antigen binding pocket. Addition of various signal sequences allows the scFv to be targeted to different organelles within the cell, or to be secreted. Addition of the light chain constant region (Ck) allows dimerization via disulphide bonds, giving increased stability and avidity. However, there is evidence that scFvs spontaneously multimerize, with the extent of aggregation (presumably via exposed hydrophobic surfaces) being dependent on the length of the glycine-serine linker.

The variable regions for constructing the scFv are obtained as follows. Using a monoclonal antibody against the target of interest, it is a simple procedure to use RT-PCR to clone out the variable regions from mRNA extracted from the parent hybridoma. Degenerate primers targeted to the relatively invariant framework regions can be used. Expression constructs are available with convenient cloning sites for the insertion of the cloned variable regions.

5. siRNA

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery et al., 1999; Montgomery et al., 1998; Sharp and Zamore, 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, *C. elegans, Trypanasoma, Drosophila*, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998).

The making of siRNAs has been mainly through direct chemical synthesis; through processing of longer, double-stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides +3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25-100 nM, but concentrations of about 100 nM have achieved effective suppression of expression in mammalian cells. siRNAs have been most effective in mammalian cell culture at about 100 nM. In several instances, however, lower concentrations of chemically synthesized siRNA have been used (Caplen, et al., 2000; Elbashir et al., 2001).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25 mer lengths with the endogenous nuclease complex that converts long dsRNAs to siRNAs in vivo. They do not describe or present data for synthesizing and using in vitro transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

6. Vectors

In accordance with the present invention, both stimulatory and inhibitory genes may be provided to a cancer cell and expressed therein. Stimulatory genes are generally simply copies of the gene of interest, although in some cases they may be genes, the expression of which direct the expression of the gene of interest. Inhibitory genes, discussed above, may include expression constructs for antisense molecules, ribozymes, interfering RNAs or single-chain antibodies.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 1 lists non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| α$_1$-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |

TABLE 1-continued

Promoter and/or Enhancer

| Promoter/Enhancer | References |
| --- | --- |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), DIA dopamine receptor gene (Lee et al., 1997), insulin-like growth factor II (Wu et al., 1997), and human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference).

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system as it has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid (e.g., one encoding gene of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

5. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

7. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989; Nabel and Baltimore, 1987), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. No. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into Xenopus oocytes (Harland and Weintraub, 1985).

b. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

C. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

d. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

e. Sonication Loading

Additional embodiments of the present invention include the introduction of a nucleic acid by direct sonic loading. LTK− fibroblasts have been transfected with the thymidine kinase gene by sonication loading (Fechheimer et al., 1987).

f. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

g. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

h. Microprojectile Bombardment

Microprojectile bombardment techniques can be used to introduce a nucleic acid into at least one, organelle, cell, tissue or organism (U.S. Pat. Nos. 5,550,318, 5,538,880, 5,610,042, and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

VII. PHARMACEUTICAL FORMULATIONS AND ROUTES OF ADMINISTRATION

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions.

Administration of these compositions according to the present invention will be via any common route so long as the target tissue is available via that route. This includes intradermal, subcutaneous, intramuscular, intraperitoneal or intravenous injection. In particular, intratumoral routes and sites local and regional to tumors are contemplated. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy administration by a syringe is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration the polypeptides of the present invention may be incorporated with excipients that may include water, binders, abrasives, flavoring agents, foaming agents, and humectants.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Materials. The MALDI matrix compound 3,5-dimethoxy-4-hydroxycinnamic acid (sinapinic acid, SA), hematoxylin, eosin, phenylmethylsulfonyl fluoride (PMSF), sodium chloride and ammonium bicarbonate were purchased from Sigma Chemical Co. (St. Louis, Mo.). Dulbecco's Modified Eagle's Medium (DMEM) was from Life Technologies, Inc. (Rockville, Md.) and fetal bovine serum (FBS) was from Gemini Bio-Products (Woodland, Calif.). T-PER extraction buffer was purchased from Pierce Biotechnology, Inc. (Rockford, Ill.). Sucrose, ammonium acetate and ultrapure Tris were obtained from J. T. Baker (Phillipsburg, N.J.). Sequencing grade trifluoroacetic acid (TFA) was from Burdick and Jackson (Muskegon, Mich.). HPLC grade acetonitrile was purchased from EM Science (Merck, Darmstadt, Germany). Sequencing grade trypsin was from Promega (Madison, Wis.) and Anti-PEA-15 from Santa Cruz Biotechnology, Inc. (Santa Cruz, Calif.).

Collecting and Processing Clinical Material and Patient Information. Tissues were obtained, with informed consent and IRB approval, from patients undergoing tumor resection or other surgical procedures at Vanderbilt University Medical Center, Cleveland Clinical Foundation and the National Institutes of Health. A total of 162 tissue samples from 127 patients including 19 patients undergoing resective surgery for non-neoplastic disease, 29 grade II, 22 grade III, and 57 grade IV glioma patients were analyzed. Patient information was collected including gender, age, treatment received before and after surgery, extent of surgery, current status (alive, alive with progressive disease, deceased and cause of death), and survival from the time of original pathological diagnosis. Samples were collected at the time of surgery, immediately snap-frozen in liquid nitrogen, and stored at −80° C. until analysis. Histopathological diagnoses were made by a neuropathologist, blinded to the original clinical diagnosis, from subsequent H & E stained sections according to the 2000 WHO classification (Klieihues and Cavenee, 2000) as previously described (Schwatrtz et al., 2004).

Samples were prepared for MALDI analysis as described previously (Schwatrtz et al., 2004; Schwartz et al., 2003). Briefly, frozen tissues were sectioned and transferred to MALDI target plates. Matrix droplets (0.1 µl saturated SA in 50:50 acetonitrile:0.1% TFA in water, v/v) were blindly deposited on the surface of the sample, and the sections were dried. Optical section images were taken to align MS analysis regions with cellular morphology determined by histology. Samples were analyzed in a blinded fashion without knowledge of histological diagnosis or clinical data.

Mass Spectrometry Analysis and Data Processing. Each matrix droplet was analyzed on a MALDI TOF (time-offlight) Voyager DE-STR mass spectrometer (Applied Biosystems, Foster City, Calif.) as described previously (Schwatrtz et al., 2004). Spectra were internally mass calibrated using the singly- and doubly-charged ions for α-hemoglobin (m/z 7564.2 and 15127.4 respectively), ubiquitin (m/z 8565.8), and thymosin β4 (m/z 4964.5, previously identified in human glioblastoma xenographs (Stoeckli et al., 2001). Mass spectra were baseline corrected, smoothed, and normalized. The peak lists from each individual biopsy or patient, depending on the analysis approach, were averaged to generate one general protein profile.

Statistical Data Analysis. Two independent supervised methods, symbolic discriminant analysis (SDA) (Moore et al., 2002) and the weighted flexible compound covariate method (WFCCM) (Shyr and KyungMann, 2003), were used to analyze the protein profiles. SDA applies genetic programming to determine discriminatory signals and builds functions using these signals that distinguish sample populations based on their classification. WFCCM applies multiple statistical tests to determine discriminatory markers. A linear combination of these markers is then generated that differentiates the sample groups. Further information is included in the supplementary data.

Protein Marker Identification. Two samples were used for protein identification, a glioma cell line and a human glioma sample. The glioblastoma cell line, U118 MG, (American Type Culture Collection, Manassas, Va.) was cultured in DMEM supplemented with 10% FBS and harvested using an extraction buffer (0.25 M sucrose, 0.01 M Tris-HCL and 0.1 mM PMSF, pH 7.6 at 4° C.). A cell aliquot was mixed 1:1 (v/v) with the extraction buffer, homogenized in an ice-chilled Duall homogenizer and centrifuged at 10,000 g for 10 min at 4° C. The supernatant was collected for protein identification. A glioblastoma (grade IV glioma) tissue was collected at the time of surgery, frozen and stored at −80° C. The tissue was homogenized in T-PER extraction buffer (50 mg of tissue per 1 mL of T-PER) in an ice-chilled Duall homogenizer and centrifuged at 16,000 g for 30 min at 4° C. The supernatant was collected for protein identification.

Both samples were separated in two-dimensions, first by ion exchange chromatography followed by reverse-phase high-performance liquid chromatography (HPLC). The cell line supernatant was separated by anion exchange chromatography using a HiTrap Q HP anion exchange column (Amersham Biosciences, Uppsala, Sweden) and a NaCl gradient (0.05 M, 0.1 M, 0.15 M, 0.2 M, 0.25 M, 0.3 M, 0.35 M, 0.45 M, 0.55 M, and 1 M NaCl) based on the extraction solution. HPLC separation for selected fractions was achieved over a Vydac (Hesperia, Calif.) 214MS52 reverse phase C4 column (5 µm particles, 2.1 mm×25 cm) at 40° C. using a linear gradient of 5% B to 20% B over 11 min, 20% B to 30% B over 15 min, 30% B to 55% B over 90 min, and 55% B to 95% B over 10 min. For fraction separation, solvent A was 0.1% TFA and solvent B was 0.1% TFA in acetonitrile. The tissue sample supernatant was separated by cation exchange chromatography using a HiTrap SP HP cation exchange column (Amersham Biosciences, Uppsala, Sweden) with a linear gradient of 0% B to 100% B over 15 min, where A was 10 mM ammonium acetate and B was 1 M NaCl in 10 mM ammonium acetate, pH 3.8 at room temperature. Selected fractions were separated over a Vydac (Hesperia, Calif.) 214MS5115 reverse phase C4 column (5 gm particles, 1 mm×15 cm) at 40° C. using a linear gradient of 5% B to 25% B over 5 min, 25% B to 60% B over 50 min, and 60% B to 95% B over 20 min. Fractions were analyzed by MALDI MS for the markers of interest after each separation. HPLC fractions of interest were reconstituted in 0.1 M ammonium bicarbonate and digested with trypsin (1:50, trypsin:protein, w/w; 37° C.; 16-20 hrs). Digested fragments were analyzed using either an Applied Biosystems 4700 MALDI TOF/TOF mass spectrometer (Foster City, Calif.) or a ThermoLTQ ion trap mass spectrometer equipped with a Thermo Surveyor LC pump and a microelectrospray source (Thermo Electron, San Jose, Calif.).

MS and MS-MS spectra from MALDI TOF/TOF analysis were collected and the proteins were identified as previously described (Friedman et al., 2004). The data were searched against the human NCBI database using the Mascot (world wide web at at matrixscience.com) database search algorithm. A significance cut-off score of 65 was used. Analysis on the ThermoLTQ mass spectrometer was performed using one full MS scan followed by three MS-MS scans of the three most intense ions. MS-MS spectra were searched against the human database using SEQUEST (Thermo Electron, San Jose, Calif.) and the Sequest search outputs were filtered using a custom-designed software tool called CHIPS (Complete Heirarchical Integration of Protein Searches) using the following filtering criteria: cross correlation ($X_{corr}$) value of >1.0 for singly charged ions, >1.8 for doubly charged ions, and >2.5 for triply charged ion. In addition, a RSp (ranking of preliminary score) value of <5 and a Sp value (preliminary score) >350 were required for positive peptide identifications. A minimum of two peptide matches and a positive correlation between the m/z ratio detected and the MW of the intact protein (including post-translational modifications) were also required for protein identification.

Immunohistochemistry. For immunofluorescence histochemistry, 18 µm thick sections were cut on a cryostat and incubated for 24 hours with PEA-15 antibodies (1:1000). The sections were washed and incubated with Cy3-conjugated anti-mouse secondary antibodies (1:1600; Jackson ImmunoResearch), washed, mounted, and coverslipped.

Example 2

Results

Figure 2:
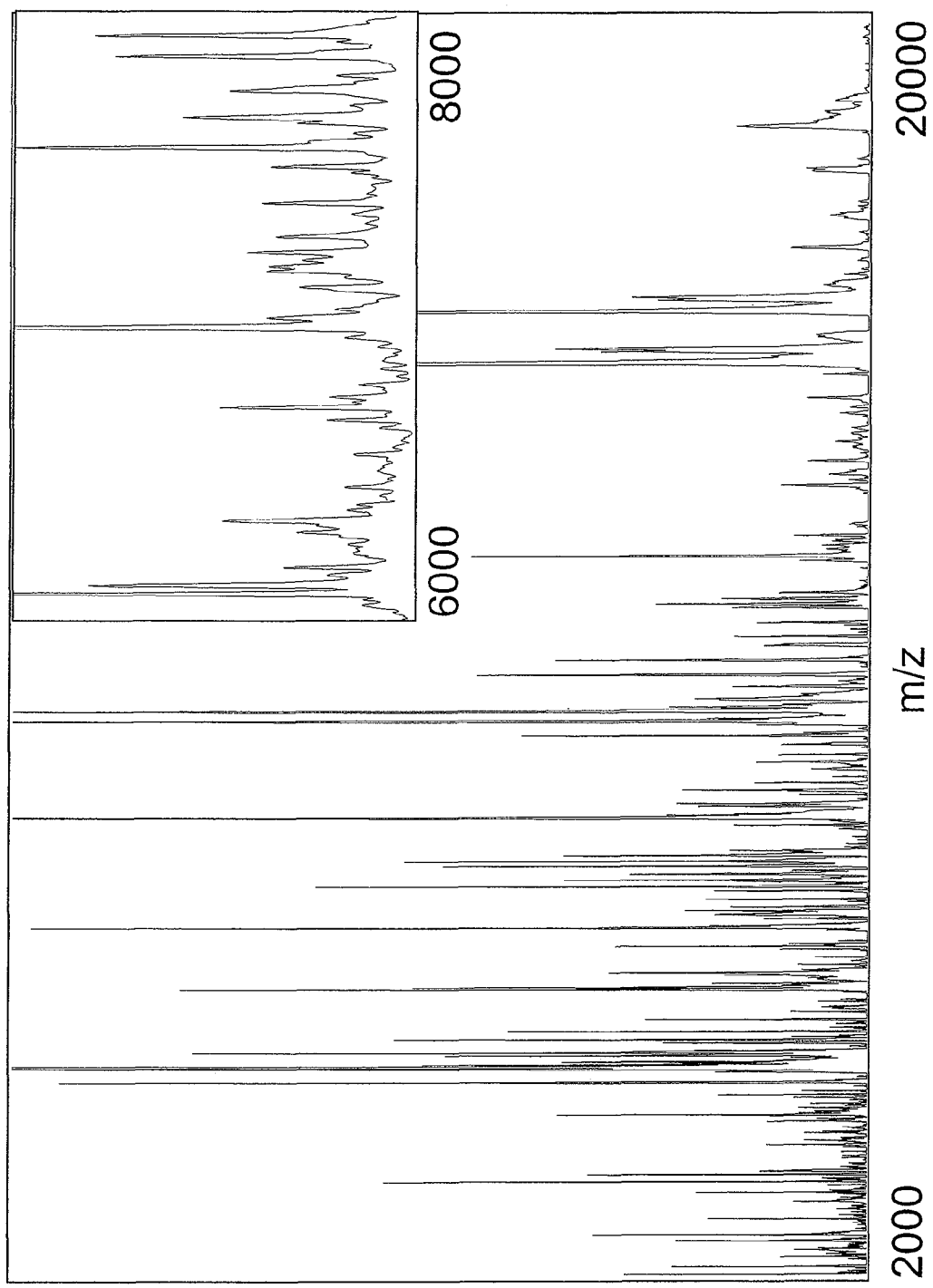
FIG. 2: Protein profile generated from direct MS analysis of a matrix droplet deposited on a 12 µm human glioma section. The intensity scale has been expanded to display low intensity ion signals. The inset, displaying the m/z range 6000 to 8000, demonstrates the complexity of the data collected from tissue samples. Over thirty ion signals can be recognized in the inset alone; over 500 signals were observed across the entire spectrum.

Mass Spectrometric Profiling of Human Brain Tissues. A total of 162 tissue samples from 127 patients (108 glioma and 19 non-tumor patients) were collected and analyzed by mass spectrometry. The general protocol is presented (FIG. 1). Tissue sections were coated with matrix droplets (typically 5-10 droplets were deposited on each section) and each droplet was directly analyzed by MALDI MS; serial sections were collected and stained with hematoxylin and eosin for histopathology. Over 1000 individual mass spectra, representing non-tumor cell populations from non-tumor patients or tumor cell populations from glioma patients, were used for comparative analysis. Between 300 and 500 individual protein signals in the mass/charge (m/z) range of 2,000 to 70,000 were detected; an example of the protein profile complexity, generated by MS analysis of a 12 µm human glioma section, is presented (FIG. 2). The intensity scale was expanded to display low intensity ion signals. The inset, displaying the m/z range 6000 to 8000, further demonstrates the complexity of the data collected. The spectra were processed and multiple spectra were averaged to generate one peak list per patient or tissue sample, depending on the statistical analysis performed. To determine the variability of our tissue profiling approach, the average intra-class agreement rate (protein pattern variations within a patient sample) was measured to be 91.3%±2.6% (95% CI: 87.2%, 95.4%). This measurement suggests a relative consistency, spectrum-to-spectrum, within a given tissue sample.

Correlating Protein Pattern Changes to Glioma Classifications. Initial data analysis focused on verifying that direct-tissue MALDI mass spectrometric analysis could be used for tissue classification. Supervised classification analysis was performed to identify tumor classification-distinctive biomarker patterns, verified by histology. Data was processed, averaged by biopsy, and grouped into one of four categories: non-tumor tissue (26 samples), grade II tumor (35 samples), grade III tumor (28 samples) and grade IV tumor (73 samples). Non-tumor tissue refers to samples collected from patients undergoing surgical resection for non-neoplastic processes. For statistical analysis, biopsies were separated into training and testing data sets, consisting of ⅔ and ⅓ of the samples per classification, respectively.

Pairwise comparisons were performed on the training set to identify a subset of differentially expressed protein signals that best separated each classification: non-tumor vs. grades II, III and IV biopsies; non-tumor vs. each individual tumor grade; grade II vs. grade III; grade II vs. grade IV; grade III vs. grade IV; and grade II, III vs. grade IV. Two independent methods were utilized for data analysis: symbolic discriminant analysis (SDA) (Moore et al., 2002) and the weighted flexible compound covariate method (WFCCM) (Shyr and KyungMann, 2003). SDA utilizes genetic programming to build functions, based on determined discriminatory signals, which distinguish sample classifications. WFCCM generates a model, based on a linear combination of statistically-determined discriminatory markers, which distinguishes sample groups.

For each analysis approach, a model was defined that best classified samples in the training data set. Based on the model, each patient was assigned a score using the expression, or signal intensity, of the determined biomarker signals; the accuracy of this classification scheme was verified on a blind data set (testing data set). The results from these analyses are summarized (Table 2). Classification and prediction accuracies are defined as the number of samples in the training and testing data sets, respectively, correctly classified. Biopsy protein patterns reflect a strong separation between tumor and non-tumor tissues that extends to individual tumor grades. In all cases, non-tumor tissues could be distinguished from gliomas with >92% classification accuracy. When comparing gliomas of different grades, the best separation was seen when comparing grade II and grade IV tumors (>93% classification accuracy), with slightly lower values for the grade III vs. grade IV and grade II, III vs. grade IV. The most difficult comparison was between grade II and grade III, which recapitulates the clinical situation. Accuracy limitations in protein profiling are due, in part, to the infiltrative nature of these tumors, the heterogeneous nature of the cells that comprise gliomas, and some methodological limitations. Nonetheless, the results compare favorably to studies of inter-class observer variability in pathology and neuropathology (Aldape et al., 2000; Castillo et al., 2004).

TABLE 2

| Analysis | Data Set (# Biopsies Training; Testing Set) | SDA | | | WFCCM | | |
|---|---|---|---|---|---|---|---|
| | | No. Biomarkers Determined | Classification Accuracy (%) | Prediction Accuracy (%) | No. Biomarkers Determined | Classification Accuracy (%) | Prediction Accuracy (%) |
| NT/T | 18/91; 8/45 | 2 | 92 | 89 | 28 | 96 | 92 |
| NT/TII | 18/24; 8/11 | 2 | 92 | 84 | 26 | 100 | 84 |
| NT/TIII | 18/17; 8/11 | 4 | 94 | 95 | 38 | 97 | 89 |
| NT/TIV | 18/50; 8/23 | 2 | 96 | 84 | 42 | 99 | 87 |
| TII/TIII | 24/17; 11/11 | 2 | 76 | 77 | 61 | 88 | 50 |
| TII/TIV | 24/50; 11/23 | 3 | 93 | 82 | 17 | 97 | 82 |
| TIII/TIV | 17/50; 11/23 | 4 | 85 | 80 | 32 | 96 | 76 |
| TII, III/TIV | 41/50; 22/73 | 1 | 79 | 80 | 62 | 93 | 78 |

Interestingly, both analyses exhibited similar abilities in segregating the individual classifications. Models from SDA and WFCCM performed well in distinguishing non-tumor from tumor and generally separating individual tumor grades, but performed poorly in segregating grade II from grade III. While the marker patterns determined by SDA and WFCCM were distinct, 35% of the classification-specific markers determined using SDA were also selected by WFCCM. These results suggest that classification based on protein profiling may be independent of the statistical analysis technique used.

An independent agglomerative hierarchical clustering algorithm verified the statistically significant discriminator protein patterns, determined by WFCCM, in the training cohort for each of the classifications performed. The results of three of these, NT vs. T, NT vs. $T_{IV}$ and $T_{II}$ vs. $T_{IV}$ are shown (FIGS. 3A, 3B and 3C, respectively). Clustering patterns reflect the strong correlation between the MS protein profile and the tissue classifications.

Correlating Protein Pattern Changes to Glioma Patient Survival. Statistical analysis was then applied to the entire tumor data set of 108 glioma patients, with the spectra averaged by patient, to identify biomarker patterns that correlate to patient survival trends. Using WFCCM, a summary survival score was determined for each patient based on the statistically-determined significant protein signals. Patients were then separated into short-term and long-term prognostic groups using a sensitivity analysis according to their correlated protein and survival patterns (FIGS. 4A-B). A proteomic pattern of 24 distinct MS signals distinguished patients based on survival trends from the time of pathological diagnosis into two groups, a short-term (STS, mean survival <15 months) and a long-term (LTS, mean survival >90 months) survival group. Seventeen of these markers were not determined as tumor or tumor-grade specific discriminatory markers in the previous analysis. Survival signal differences include an overexpression of m/z 9747 and 10092 in the STS group and an overexpression of m/z 10262 in the LTS group. Within the total tumor patient population, analysis identified 52 patients in the STS prognostic group and 56 patients in the LTS prognostic group, with P<0.0001. Univariate analysis demonstrated a positive correlation (P<0.01) between advanced patient age, increasing tumor grade, tumors with an astrocytic lineage and shorter survival trends. Taking these factors in account, a multivariate Cox proportional hazards model showed a strong correlation between the MS protein pattern and patient survival after adjustment for patient age, gender, tumor subtype, tumor grade, extent of tumor resection and the use of radiation and chemotherapy treatments pre- and post-surgery. Therefore, the protein pattern served as an independent indicator of patient survival. The key patient survival variables are shown in a modified model (Table 3). Survival analysis of the glioma population from the time of surgery, in which the analyzed sample was resected, was also performed with similar results (data not shown).

TABLE 3

| Variable | H.R. | P-value | 95% CI |
|---|---|---|---|
| Grade II, III and IV Gliomas | | | |
| MS Protein Pattern | 1.002 | <0.0001 | (1.001, 1.003) |
| Age | 1.034 | 0.0177 | (1.006, 1.062) |
| Gender | 0.926 | 0.8366 | (0.445, 1.928) |
| Chemotherapy | 0.296 | 0.0184 | (0.107, 0.814) |
| Radiation | 1.402 | 0.4697 | (0.561, 3.500) |
| Tumor Grade | 4.581 | 0.0100 | (1.440, 14.575) |
| Grade IV Gliomas | | | |
| MS Protein Pattern | 1.014 | 0.0001 | (1.007, 1.021) |
| Age | 1.063 | 0.0006 | (1.026, 1.021) |
| Gender | 1.551 | 0.3485 | (0.620, 3.879) |
| Chemotherapy | 0.898 | 0.8349 | (0.327, 2.467) |
| Radiation | 0.799 | 0.6728 | (0.281, 2.268) |

Glioblastoma multiforme (GBM), the most common and malignant form of glioma, is also one of the most rapidly fatal of all human malignancies; median survival after diagnosis for these tumors is measured in months. For patients with a GBM, age, clinical performance status and extent of surgical resection are the principal, well-validated prognostic variables. WFCCM analysis was used to determine whether protein patterns could further differentiate patients based on survival from the time of GBM presentation. A proteomic pattern of 2 distinct MS signals was identified that segregated the patients into a STS (average survival, 10.9 months) and LTS group (average survival, 16.8 months). Neither of these signals was identified as a significant discriminatory marker in the previous analyses. A total of 28 of the 57 patients were classified into the STS group and 29 patients in the LTS group (P<0.0001). While an independent correlation existed between increasing patient age and shorter survival trends, the protein pattern performed as a powerful, independent predictor of patient survival. A multivariate Cox proportional hazards model demonstrated a strong correlation between the MS protein pattern and patient survival after adjustment for patient age, gender, extent of tumor resection, histological subtype, and the use of radiation and chemotherapy treatments. A modified form of this model is presented (Table 3).

Identifying Glioma Biomarkers. Discriminatory protein identification was confirmed using two protein sources, the malignant human glioma cell line, U118 MG, and a primary human grade IV glioblastoma sample. Both the cells and the tissue sample were homogenized and proteins separated using a two-dimensional LC approach, consisting of an ion exchange separation followed by reverse-phase HPLC separation. Fractions were monitored by MALDI MS during separation for the m/z signals of interest. Selected fractions were digested and analyzed by either an Applied Biosystems 4700 MALDI TOF/TOF (Foster City, Calif.) mass spectrometer or a ThermoLTQ ion trap mass spectrometer (Thermo Electron, San Jose, Calif.). Six proteins were identified including: calcyclin (m/z 10092), dynein light chain 2 (m/z 10262), calpactin I light chain (m/z 11073), astrocytic phosphoprotein PEA-15 (m/z 15035) (FIG. 5C), fatty acid binding protein 5 (m/z 15076) and tubulin-specific chaperone A (m/z 17268). Calcyclin, calpactin I light chain, and tubulin-specific chaperone A were identified as overexpressed in grade IV gliomas. On the other hand, astrocytic phosphoprotein PEA-15 was overexpressed in grade II and grade III tumors as opposed to grade IV gliomas and fatty acid binding protein 5 was overexpressed in grade III tumors as opposed to grade IV. Calcyclin and dynein light chain 2 also discriminated between glioma survival subgroups with calcyclin predominant in STS patients and dynein light chain 2 overexpressed in LTS patients. The presence and relative expression levels for several of these proteins were verified by immunohistochemistry on intact tumor sections. For example, PEA-15 is demonstrated to be in higher abundance in grade II astrocytomas compared to grade IV glioblastomas as recognized by the antibody staining pattern (FIG. 5A). This increase in protein expression correlates well with the presence of a mass spectrometric signal at m/z 15035 collected from a consecutive grade II tissue section as opposed to the loss of this signal in the grade IV section (FIG. 5B).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,415,723
U.S. Pat. No. 4,415,723
U.S. Pat. No. 4,458,066
U.S. Pat. No. 4,458,066
U.S. Pat. No. 4,683,195
U.S. Pat. No. 4,683,202
U.S. Pat. No. 4,684,611
U.S. Pat. No. 4,797,368
U.S. Pat. No. 4,800,159
U.S. Pat. No. 4,883,750
U.S. Pat. No. 4,952,500
U.S. Pat. No. 5,139,941
U.S. Pat. No. 5,242,974
U.S. Pat. No. 5,279,721
U.S. Pat. No. 5,302,523
U.S. Pat. No. 5,322,783
U.S. Pat. No. 5,384,253
U.S. Pat. No. 5,384,261

U.S. Pat. No. 5,405,783
U.S. Pat. No. 5,412,087
U.S. Pat. No. 5,424,186
U.S. Pat. No. 5,429,807
U.S. Pat. No. 5,436,327
U.S. Pat. No. 5,445,934
U.S. Pat. No. 5,464,765
U.S. Pat. No. 5,472,672
U.S. Pat. No. 5,527,681
U.S. Pat. No. 5,529,756
U.S. Pat. No. 5,532,128
U.S. Pat. No. 5,538,877
U.S. Pat. No. 5,538,880
U.S. Pat. No. 5,545,531
U.S. Pat. No. 5,550,318
U.S. Pat. No. 5,554,501
U.S. Pat. No. 5,556,752
U.S. Pat. No. 5,561,071
U.S. Pat. No. 5,563,055
U.S. Pat. No. 5,571,639
U.S. Pat. No. 5,580,859
U.S. Pat. No. 5,589,466
U.S. Pat. No. 5,591,616
U.S. Pat. No. 5,593,839
U.S. Pat. No. 5,599,695
U.S. Pat. No. 5,610,042
U.S. Pat. No. 5,624,711
U.S. Pat. No. 5,656,610
U.S. Pat. No. 5,658,734
U.S. Pat. No. 5,700,637
U.S. Pat. No. 5,702,932
U.S. Pat. No. 5,736,524
U.S. Pat. No. 5,757,994
U.S. Pat. No. 5,757,994
U.S. Pat. No. 5,780,448
U.S. Pat. No. 5,788,166
U.S. Pat. No. 5,789,215
U.S. Pat. No. 5,795,715
U.S. Pat. No. 5,838,002
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,336
U.S. Pat. No. 5,882,864
U.S. Pat. No. 5,889,136
U.S. Pat. No. 5,889,136
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,565
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,986,258
U.S. Pat. No. 5,986,258
U.S. Pat. No. 5,994,136
U.S. Pat. No. 5,994,624
U.S. Pat. No. 6,004,755
U.S. Pat. No. 6,013,516
U.S. Pat. No. RE 35,413
Abbondanzo, *Ann Diagn Pathol,* 3(5):318-327, 1999.
Aldape et al., *Cancer,* 88:2342-2349, 2000.
Alizadeh et al., *Nature* 403 (6769), 503-511, 2000.
Allred et al., *Arch Surg,* 125(1):107-13, 1990.
Almendro et al., *J Immunol.,* 157:5411-5421, 1996.
Angel et al., *Cell,* 49:729, 1987b.
Angel et al., *Mol. Cell. Biol.,* 7:2256, 1987a.
Antibodies: A Laboratory Manual, Cold Spring Harbor Laboratory, Cold Spring Harbor Press, Cold Spring Harbor, New York, 1988.
Atchison and Perry, *Cell,* 46:253, 1986.
Atchison and Perry, *Cell,* 48:121, 1987.
Ausubel et al., In: *Current Protocols in Molecular Biology,* John, Wiley & Sons, Inc, New York, 1994.
Bahr et al., *J. Mass Spectrom.,* 32:1111-1116, 1997.
Baichwal and Sugden, In: *Gene Transfer,* Kucherlapati (ed.), New York, Plenum Press, 117-148, 1986.
Banerji et al., *Cell,* 27(2 Pt 1):299-308, 1981.
Banerji et al., *Cell,* 33(3):729-740, 1983.
Bentzley et al., *Anal Chem.,* 68(13):2141-2146, 1996.
Berkhout et al., *Cell,* 59:273-282, 1989.
Bittner et al., *Nature* 406 (6795), 536-40, 2000.
Blanar et al., *EMBO J.,* 8:1139, 1989.
Blomer et al., *J. Virol.,* 71(9):6641-6649, 1997.
Bodine and Ley, *EMBO J.,* 6:2997, 1987.
Boshart et al., *Cell,* 41:521, 1985.
Bosher and Labouesse, *Nat. Cell. Biol.,* 2:E31-E36, 2000.
Bosze et al., *EMBO J.,* 5(7):1615-1623, 1986.
Braddock et al., *Cell,* 58:269, 1989.
Bronckart et al., *Histol. Histopathol.,* 16:707-712, 2001.

Brown et al., *Immunol Ser,* 53:69-82, 1990.
Bucknall et al., *J. Am. Soc. Mass Spectrom.,* 13(9):1015-1027, 2002.
Bulla and Siddiqui, *J. Virol.,* 62:1437, 1986.
Camby et al., *Brain Pathol.,* 9:1-19, 1999.
Campbell and Villarreal, *Mol. Cell. Biol.,* 8:1993, 1988.
Campere and Tilghman, *Genes and Dev.,* 3:537, 1989.
Campo et al., *Nature,* 303:77, 1983.
Caplen et al., Gene, 252(1-2):95-105, 2000.
Caprioli et al., *Anal. Chem.,* 69:4751, 1997.
Carbonelli et al., *FEMS Microbiol Lett,* 177(1):75-82, 1999.
Castillo et al., *Neuroepidemiology,* 23:85-93, 2004.
Celander and Haseltine, *J. Virology,* 61:269, 1987.
Celander et al., *J. Virology,* 62:1314, 1988.
Chamberlan et al., In: *PCR Protocols,* eds. Innis, Gelfand, Sninsky, White (Academic Press, NY, 272-281, 1990.
Chandler et al., *Cell,* 33:489, 1983.
Chandler et al., *Proc Natl Acad Sci USA,* 94(8):3596-601, 1997.
Chang et al., *Mol. Cell. Biol.,* 9:2153, 1989.
Chatterjee et al., *Proc. Natl. Acad. Sci. USA,* 86:9114, 1989.
Chaurand et al., *Anal Chem.,* 71(23):5263-5270, 1999.
Chaurand et al., *Anal Chem.,* 71(23):5263-5270, 1999.
Chen and Okayama, *Mol. Cell. Biol.,* 7(8):2745-2752, 1987.
Chen et al., *Nat. Biotechnol.,* 19:537-542, 2001.
Choi et al., *Cell,* 53:519, 1988.
Cocea, *Biotechniques,* 23(5):814-816, 1997.
Cohen et al., *J. Cell. Physiol.,* 5:75, 1987.
Condorelli et al., *Embo J.,* 17:3858-3866, 1998.
Condorelli et al., *Oncogene,* 18:4409-4415, 1999.
Costa et al., *Mol. Cell. Biol.,* 8:81, 1988.
Cotten et al., *Proc Natl Acad Sci USA,* 89(13):6094-6098, 1992.
Coupar et al., *Gene,* 68:1-10, 1988.
Cripe et al., *EMBO J.,* 6:3745, 1987.
Culotta and Hamer, *Mol. Cell. Biol.,* 9:1376, 1989.
Curiel, *Nat Immun,* 13(2-3): 141-64, 1994.
Dandolo et al., *J. Virology,* 47:55-64, 1983.
De Jager et al., *Semin Nucl Med* 23(2): 165-179, 1993.
De Villiers et al., *Nature,* 312(5991):242-246, 1984.
Deschamps et al., *Science,* 230:1174-1177, 1985.
Desiderio et al., *J. Mass Spectrom.,* 35(6):725-733, 2000.
Desiderio et al., *Methods Mol. Biol.,* 61:57-65, 1996.
Doolittle et al., *Methods Mol Biol.,* 109:215-237, 1999.
Dougherty, *Comparative and Functional Genomics* 2:28-34, 2001.
Duncan et al., *Rapid Commun. Mass Spectrom.,* 7(12):1090-1094, 1993.
Edbrooke et al., *Mol. Cell. Biol.,* 9:1908, 1989.
Edlund et al., *Science,* 230:912-916, 1985.
Elbashir et al., *Genes Dev.,* 5(2):188-200, 2001.
Elbashir et al., *Nature,* 411(6836):494-498, 2001.
El-Rifai et al., *Cancer Res.,* 62:6823-6826, 2002.
European Application No. 0 364 255
European Application No. 320 308
European Application No. EPO 0273085
European Application No. GB 2 202 328
European Application No.329 822
Faulstich et al., *Anal. Chem.,* 69(21):4349-4353, 1997.
Fechheimer et al., *Proc. Nat'l Acad. Sci. USA,* 84:8463-8467, 1987.
Feng and Holland, *Nature,* 334:6178, 1988.
Fenn et al., *Science,* 246(4926):64-71, 1989.
Firak and Subramanian, *Mol. Cell. Biol.,* 6:3667, 1986.
Fire et al., *Nature,* 391(6669):806-811, 1998.
Foecking and Hofstetter, *Gene,* 45(1):101-105, 1986.
Fraley et al., *Proc. Nat'l Acad. Sci. USA,* 76:3348-3352, 1979.
Friedman et al., *Proteomics,* 4:793-811, 2004.
Friedmann, *Science,* 244:1275-1281, 1989.
Frohman, In: *PCR Protocols: A Guide To Methods And Applications,* Academic Press, N.Y., 1990.
Fujita et al., *Cell,* 49:357, 1987.
Ghosh and Bachhawat, In: *Liver Diseases, Targeted Diagnosis and Therapy Using Specific Receptors and Ligands.* Wu et al., eds., Marcel Dekker, New York, pp. 87-104, 1991.
Gilles et al., *Cell,* 33:717, 1983.
Gloss et al., *EMBO J.,* 6:3735, 1987.
Gobom et al., *Anal. Chem.,* 72(14):3320-3326, 2000.
Godbout et al., *Mol. Cell. Biol.,* 8:1169, 1988.
Golub et al., *Science* 286, 531-537, 1999.
Goodbourn and Maniatis, *Proc. Natl. Acad. Sci. USA,* 85:1447, 1988.
Goodbourn et al., *Cell,* 45:601, 1986.
Gopal, *Mol. Cell Biol.,* 5:1188-1190, 1985.
Graham and Van Der Eb, *Virology,* 52:456-467, 1973.
Greene et al., *Immunology Today,* 10:272, 1989
Grishok et al., *Science,* 287:2494-2497, 2000.
Grosschedl and Baltimore, *Cell,* 41:885, 1985.
Grunhaus et al., *Seminar in Virology,* 200(2):535-546, 1992.
Gulbis and Galand, *Hum Pathol* 24(12):1271-1285, 1993.
Harland and Weintraub, *J. Cell Biol.,* 101:1094-1099, 1985.
Haslinger and Karin, *Proc. Natl. Acad. Sci. USA,* 82:8572, 1985.
Hauber and Cullen, *J. Virology,* 62:673, 1988.
Hen et al., *Nature,* 321:249, 1986.
Hensel et al., *Lymphokine Res.,* 8:347, 1989.
Herr and Clarke, *Cell,* 45:461, 1986.
Hirochika et al., *J. Virol.,* 61:2599, 1987.
Hirsch et al., *Mol. Cell. Biol.,* 10:1959, 1990.
Holbrook et al., *Virology,* 157:211, 1987.
Horak et al., *Rapid Commun. Mass Spectrom.,* 15(4):241-248, 2001.
Horlick and Benfield, *Mol. Cell. Biol.,* 9:2396, 1989.
Horwich et al., *Virol.,* 64:642-650, 1990.
Huang et al., *Cell,* 27:245, 1981.
Hug et al., *Mol. Cell. Biol.,* 8:3065, 1988.
Hwang et al., *Mol. Cell. Biol.,* 10:585, 1990.
Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Innis et al., *Proc. Natl. Acad. Sci. USA,* 85(24):9436-9440, 1988.
Inouye and Inouye, *Nucleic Acids Res.,* 13: 3101-3109, 1985.
Jakobovits et al., *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Jespersen et al., *Anal Chem.,* 71(3):660-666, 1999.
Jiang et al., *J. Agric. Food Chem.,* 48:3305, 2000.
Johnson et al., *Mol. Cell. Biol.,* 9:3393, 1989.
Kabarle et al., *Anal. Chem.* 65(20):972A-986A, 1993.
Kadesch and Berg, *Mol. Cell. Biol.,* 6:2593, 1986.
Kaeppler et al., *Plant Cell Reports* 9: 415-418, 1990.
Kanazawa et al., *Biol. Pharm. Bull.,* 22(4):339-346, 1999.
Kaneda et al., *Science,* 243:375-378, 1989.
Karin et al., *Mol. Cell. Biol.,*7:606, 1987.
Katinka et al., *Cell,* 20:393, 1980.
Kato et al., *J. Biol. Chem.,* 266:3361-3364, 1991.
Kawamoto et al., *Mol. Cell. Biol.,* 8:267, 1988.
Kazmaier et al., *Anesthesiology,* 89(4):831-817, 1998.
Kelleher and Vos, *Biotechniques,* 17(6): 1110-7, 1994.
Ketting et al., *Cell,* 99(2):133-141, 1999.
Kiledjian et al., *Mol. Cell. Biol.,* 8:145, 1988.
Klamut et al., *Mol. Cell. Biol.,* 10:193, 1990.

Klein et al., *Nature*, 327:70-73, 1987.
Klieihues and Cavenee, In: *World Health Organization Classification of Tumours of the Nervous System*, Lyon: WHO/IARC; 2000.
Koch et al., *Mol. Cell. Biol.*, 9:303, 1989.
Komatsu et al., *Oncology*, 63:192-200, 2002.
Kraus et al. *FEBS Lett.*, 428(3):165-170, 1998.
Kriegler and Botchan, *In: Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kwoh et al., *Proc. Nat. Acad. Sci. USA*, 86: 1173, 1989.
Lareyre et al., *J. Biol Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Laughlin et al., *J. Virol.*, 60(2):515-524, 1986.
Lebkowski et al., *Mol. Cell. Biol.*, 8(10):3988-3996, 1988.
Lee et al., *J Auton Nerv Syst.* 74(2-3):86-90, 1997.
Lee et al., *Nature*, 294:228, 1981.
Lee et al., *Nucleic Acids Res.*, 12:4191-206, 1984.
Levenson et al., *Hum Gene Ther*, 9(8):1233-6, 1998.
Levinson et al., *Nature*, 295:79, 1982.
Li et al., *Trends Biotechnol.*, 18:151, 2000.
Lin and Avery, *Nature*, 402:128-129, 1999.
Lin et al., *Mol. Cell. Biol.*, 10:850, 1990.
Lovelace et al., *J. Chromatogr.*, 562(1-2):573-584, 1991.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Lynn et al., *J. Mol. Evol.*, 48(5):605-614, 1999.
Macejak and Samow, *Nature*, 353:90-94, 1991.
Majors and Varmus, *Proc. Natl. Acad. Sci. USA*, 80:5866, 1983.
Maniatis, et al., Molecular Cloning, A Laboratory Manual, Cold Spring Harbor Press, Cold Spring Harbor, N.Y., 1989.
Mann et al., *Cell*, 33:153-159, 1983.
Marie et al., *Anal. Chem.*, 72(20):5106-5114, 2000.
Martin et al., *Cancer Res.*, 60(12):3218-3224 2000.
McLaughlin et al., *J. Virol.*, 62(6):1963-1973, 1988.
McNeall et al., *Gene*, 76:81, 1989.
Melki et al., *Biochemistry*, 35:10422-10435, 1996.
Miketova et al., *Mol. Biotechnol.*, 8(3):249-253, 1997.
Miksicek et al., *Cell*, 46:203, 1986.
Miller et al., *Am. J. Clin. Oncol.*, 15(3):216-221, 1992.
Mirgorodskaya et al., *Rapid Commun. Mass Spectrom.*, 14(14):1226-1232, 2000.
Montgomery et al., *Proc. Natl. Acad. Sci. USA*, 95:15502-15507, 1998.
Moore et al., *Genet. Epidemiol.*, 23:57-69, 2002.
Mordacq and Linzer, *Genes and Dev.*, 3:760, 1989.
Moreau et al., *Nuc. Acids Res.*, 9:6047, 1981.
Muddiman et al., *Fres. J. Anal. Chem.*, 354:103, 1996.
Mueller and Wold, *Science* 246, 780-786, 1989.
Muesing et al., *Cell*, 48:691, 1987.
Muzyczka, *Curr Top Microbiol Immunol*, 158:97-129, 1992.
Nabel and Baltimore, *Nature* 326:711-713, 1987.
Nakamnura et al., In: *Handbook of Experimental Immunology* (4th Ed.), Weir et al., (eds). 1:27, Blackwell Scientific Publ., Oxford, 1987.
Naldini et al., *Science*, 272(5259):263-267, 1996.
Nelson et al., *Anal. Chem.*, 66:1408, 1994.
Ng et al., *Nuc. Acids Res.*, 17:601, 1989.
Nguyen et al., *J. Chromatogr. A.*, 705(1):21-45, 1995.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Ohara et al., *Proc. Nat'l Acad. Sci. USA*, 86: 5673-5677, 1989.
Omirulleh et al., *Plant Mol. Biol.*, 21:415-28, 1993.
Ondek et al., *EMBO J.*, 6:1017, 1987.
Ornitz et al., *Mol. Cell. Biol.*, 7:3466, 1987.
Palmiter et al., *Nature*, 300:611, 1982.
Paskind et al., *Virology*, 67:242-248, 1975.
PCT Appln. PCT/US87/00880
PCT Appln. PCT/US89/01025
PCT Appln. WO 88/10315
PCT Appln. WO 90/07641
PCT Appln. WO 89/06700
PCT Appln. WO 00/44914
PCT Appln. WO 01/36646
PCT Appln. WO 01/68836
PCT Appln. WO 94/09699
PCT Appln. WO 95/06128
PCT Appln. WO 99/32619
Pech et al., *Mol Cell Biol.*, 9:396, 1989.
Pelletier and Sonenberg, *Nature*, 334:320-325, 1988.
Perales et al., *Proc. Nat'l Acad. Sci. USA*, 91:4086-4090, 1994.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Potter et al., *Proc. Nat'l Acad Sci. USA*, 81:7161-7165, 1984.
Puthalakath et al., *Mol. Cell*, 3:287-296, 1999.
Queen and Baltimore, *Cell*, 35:741, 1983.
Quinn et al., *Mol. Cell. Biol.*, 9:4713, 1989.
Ramos et al., *Mol. Biol. Cell*, 11:2863-2872, 2000.
Redondo et al., *Science*, 247:1225, 1990.
Reisman and Rotter, *Mol. Cell. Biol.*, 9:3571, 1989.
Resendez Jr. et al., *Mol. Cell. Biol.*, 8:4579, 1988.
Ridgeway, In: *Vectors: A survey of molecular cloning vectors and their uses*, Stoneham: Butterworth, pp. 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Roepstorff, *EXS.*, 88:81-97, 2000.
Rosen et al., *Cell*, 41:813, 1988.
Roux et al., *Proc. Nat'l Acad. Sci. USA*, 86:9079-9083, 1989.
Sakai et al., *Genes and Dev.*, 2:1144, 1988.
Sambrook et al., In: *Molecular Cloning: A Laboratory Manual*, 2nd Ed., Cold Spring Harbor Press, Cold Spring Harbor, NY, 1989.
Satake et al., *J. Virology*, 62:970, 1988.
Schaffner et al., *J. Mol. Biol.*, 201:81, 1988.
Schwartz et al., Clin. Cancer Res., 10:981-987, 2004.
Schwartz et al., *J. Mass. Spectrom.*, 38:699-708, 2003.
Searle et al., *Mol. Cell. Biol.*, 5:1480, 1985.
Sharp and Marciniak, *Cell*, 59:229, 1989.
Sharp and Zamore, *Science*, 287:2431-2433, 2000.
Sharp, *Genes Dev.*, 13:139-141, 1999.
Shaul and Ben-Levy, *EMBO J.*, 6:1913, 1987.
Sherman et al., *Mol. Cell. Biol.*, 9:50, 1989.

Shyr and KyungMann, In: *Method for classifying microarray data*, Berrar and Berrars (Eds.), Norwell: Kluwer Academic Publishers, 2003.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stoeckli et al., *Nat. Med.*, 7(4):493-496, 2001.
Stuart et al., *Nature*, 317:828, 1985.
Stulik et al., *Eur. J. Cancer*, 36:1050-1059, 2000.
Sullivan and Peterlin, *Mol. Cell. Biol.*, 7:3315, 1987.
Swartzendruber and Lehman, *J. Cell. Physiology*, 85:179, 1975.
Tabara et al., *Cell*, 99(2):123-132, 1999.
Takach et al., *J. Protein Chem.*, 16:363, 1997.
Takebe et al., *Mol. Cell. Biol.*, 8:466, 1988.
Tavernier et al., *Nature*, 301:634, 1983.
Taylor and Kingston, *Mol. Cell. Biol.*, 10: 165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (ed.), New York: Plenum Press, pp. 149-188, 1986.
Thiesen et al., *J. Virology*, 62:614, 1988.
Tonini et al., *Eur. J. Cancer*, 31A:499-504, 1995.
Tratschin et al., *Mol. Cell. Biol.*, 4:2072-2081, 1984.
Treisman, *Cell*, 42:889, 1985.
Tronche et al., *Mol Biol. Med.*, 7:173, 1990.
Trudel and Constantini, *Genes and Dev.*, 6:954, 1987.
Tsumaki et al., *J Biol Chem.* 273(36):22861-22864, 1998.
Tur-Kaspa et al., *Mol. Cell Biol.*, 6:716-718, 1986.
Tyndell et al., *Nuc. Acids. Res.*, 9:6231, 1981.
Vaarala et al., *Lab. Invest.*, 80:1259-1268, 2000.
Vannice and Levinson, *J. Virology*, 62:1305, 1988.
Vasseur et al., *Proc Natl. Acad. Sci. USA*, 77:1068, 1980.
Villanueva et al., *Enzyme Microb. Technol.*, 29:99, 1999.
Wagner et al., *Proc. Natl. Acad. Sci. USA*, 87(9):3410-3414, 1990.
Wagner et al., *Science*, 260:1510-1513, 1993.
Walker et al., *Proc. Natl. Acad. Sci. USA*, 89:392-396 1992.
Wang and Calame, *Cell*, 47:241, 1986.
Wang et al., *Anal. Chem.*, 72(21):5285-5289, 2000.
Wang et al., *J. Agric. Food. Chem.*, 47:1549, 1999.
Wang et al., *J. Agric. Food. Chem.*, 47:2009, 1999.
Weber et al., *Cell*, 36:983, 1984.
Weinberger et al. *Mol. Cell. Biol.*, 8:988, 1984.
Wilson et al., *Science*, 244:1344-1346, 1989.
Wincott et al., *Nucleic Acids Res.*, 23(14):2677-2684, 1995.
Winoto and Baltimore, *Cell*, 59:649, 1989.
Wittmann et al., *Biotechnol. Bioeng.*, 72:642, 2001.
Wong et al., *Gene*, 10:87-94, 1980.
Wu and Wu, *J. Biol. Chem.*, 262:4429-4432, 1987.
Wu and Wu, *Adv. Drug Delivery Rev.*, 12:159-167, 1993.
Wu and Wu, *Biochemistry*, 27:887-892, 1988.
Wu et al., *Anal. Chem.*, 70:456A, 1998.
Wu et al., *Biochem. Biophys. Res. Commun.*, 233(1):221-226, 1997.
Wu et al., *Biochim. Biophys. Acta*, 1466:315-327, 2000.
Yang et al., *Proc Nat'l Acad. Sci. USA*, 87:9568-9572, 1990.
Yang et al., *J. Agric. Food. Chem.*, 48:3990, 2000.
Yutzey et al. *Mol. Cell. Biol.*, 9:1397, 1989.
Zhang et al., *J. Biol. Chem.*, 279:2053-2062, 2004.
Zhao-Emonet et al., *Biochem. Biophys. Acta.*, 1442(2-3):109-19, 1998.
Zhi et al., *Int. J. Cancer*, 106:327-333, 2003.
Zhong et al., *Clin. Chem. ACTA.*, 313:147,2001.
Zufferey et al., *Nat Biotechnol*, 15(9):871-875, 1997.
Zweigenbaum et al., *Anal. Chem.*, 71(13):2294-300, 1999.
Zweigenbaum et al., *J. Pharm. Biomed. Anal.*, 23(4):723-733, 2000.

What is claimed is:

1. A method of grading a glioma comprising:
   (a) assessing a sample glioma tissue for expression of astrocytic phosphoprotein PEA-15, fatty acid binding protein 5 and tubulin-specific chaperone A;
   (b) comparing said expression to expression of astrocytic phosphoprotein PEA-15, fatty acid binding protein 5 and tubulin-specific chaperone A in known glioma or normal brain tissue; and
   (c) grading said sample glioma tissue based on the similarities and differences between said expression in said sample glioma tissue and said known glioma or normal brain tissue.

2. The method of claim 1, wherein assessing comprises immunodetection, 2-D gel electrophoresis, or mass spectrometry.

3. The method of claim 2, wherein said mass spectrometry is secondary ion mass spectrometry, laser desorption mass spectrometry, matrix assisted laser desorption mass spectrometry, or electrospray mass spectrometry.

4. The method of claim 1, further comprising obtaining said sample glioma tissue from a patient.

5. The method of claim 1, further comprising making a treatment decision for a patient from which said sample glioma tissue was obtained.

6. The method of claim 5, wherein said treatment decision involves predicting drug efficacy, drug dosing or both.

7. The method of claim 1, wherein grading comprises distinguishing grade I from grade II, grade III or grade IV glioma.

8. The method of claim 1, wherein grading comprises distinguishing grade II from grade I, grade III or grade IV glioma.

9. The method of claim 1, wherein grading comprises distinguishing grade III from grade I, grade II or grade IV glioma.

10. The method of claim 1, wherein grading comprises distinguishing grade IV from grade I, grade II, or grade III.

11. The method of claim 1, further comprising assessing one or more patient variables.

12. The method of claim 11, wherein patient variables comprise age, gender, extent of tumor resection, use of pre-surgery chemotherapy, or use of pre-surgery radiotherapy.

13. The method of claim 1, wherein step (c) comprises comparing said expression in said sample glioma tissue to known glioma tissue.

14. The method of claim 1, wherein step (c) comprises comparing said expression in said sample glioma tissue to normal brain tissue.

15. The method of claim 1, wherein step (c) comprises comparing said expression in said sample glioma tissue to known glioma tissue and normal brain tissue.

16. The method of claim 1, further comprising performing histologic analysis on said glioma tissue.

17. The method of claim 1, further comprising making a prediction of patient survival based on said grading.

18. The method of claim 1, further comprising assessing one or more of calcyclin, dynein light chain 2 and calpactin I light chain in said sample glioma tissue.

19. The method of claim 18, further comprising assessing in known glioma tissue one or more of calcyclin, dynein light chain 2 and calpactin I light chain.

20. The method of claim 18, further comprising assessing in normal brain tissue one or more of calcyclin, dynein light chain 2 and calpactin I light chain.

21. A method of diagnosing a glioma comprising:
(a) assessing a suspected glioma sample tissue for expression of astrocytic phosphoprotein PEA-15, fatty acid binding protein 5 and tubulin-specific chaperone A;
(b) comparing said expression to expression of astrocytic phosphoprotein PEA-15, fatty acid binding protein 5 and tubulin-specific chaperone A in known glioma or normal brain tissue; and
(c) diagnosing said suspected glioma sample tissue based on the similarities and differences between said expression in said suspected glioma sample tissue and said known glioma or normal brain tissue.

22. The method of claim 21, wherein assessing comprises immunodetection, 2-D gel electrophoresis, or mass spectrometry.

23. The method of claim 22, wherein said mass spectrometry is secondary ion mass spectrometry, laser desorption mass spectrometry, matrix assisted laser desorption mass spectrometry, or electrospray mass spectrometry.

24. The method of claim 21, further comprising obtaining said suspected glioma sample tissue from a patient.

25. The method of claim 21, further comprising making a treatment decision for a patient from which said suspected glioma sample tissue was obtained.

26. The method of claim 25, wherein said treatment decision involves predicting drug efficacy, drug dosing or both.

27. The method of claim 21, further comprising assessing one or more patient variables.

28. The method of claim 27, wherein patient variables comprise age, gender, extent of tumor resection, use of pre-surgery chemotherapy, or use of pre-surgery radiotherapy.

29. The method of claim 21, wherein step (c) comprises comparing said expression in said suspected glioma sample tissue to known glioma tissue.

30. The method of claim 21, wherein step (c) comprises comparing said expression in said suspected glioma sample tissue to normal brain tissue.

31. The method of claim 21, wherein step (c) comprises comparing said expression in said suspected glioma sample tissue to known glioma tissue and normal brain tissue.

32. The method of claim 21, further comprising performing histologic analysis on said suspected glioma sample tissue.

33. The method of claim 21, further comprising assessing one or more of calcyclin, dynein light chain 2 and calpactin I light chain in said suspected glioma sample tissue.

34. The method of claim 33, further comprising assessing in known glioma tissue one or more of calcyclin, dynein light chain 2 and calpactin I light chain.

35. The method of claim 33, further comprising assessing in normal brain tissue one or more of calcyclin, dynein light chain 2 and calpactin I light chain.

* * * * *

UNITED STATES PATENT AND TRADEMARK OFFICE
CERTIFICATE OF CORRECTION

PATENT NO. : 7,799,519 B2
APPLICATION NO. : 11/428755
DATED : September 21, 2010
INVENTOR(S) : Richard Caprioli It is certified that error appears in the above-identified patent and that said Letters Patent is hereby corrected as shown below:

In column 1, lines 9-11, delete paragraph and insert
--This invention was made with government support under grant numbers GM 58008 and CA 86243 awarded by the National Institutes of Health. The government has certain rights in the invention.--.

Signed and Sealed this

Thirtieth Day of November, 2010

David J. Kappos
*Director of the United States Patent and Trademark Office*